United States Patent
Brodsky et al.

(10) Patent No.: US 6,669,633 B2
(45) Date of Patent: Dec. 30, 2003

(54) UNITARY OPERATOR CONTROL FOR ULTRASONIC IMAGING GRAPHICAL USER INTERFACE

(75) Inventors: Michael Brodsky, Pepperell, MA (US); Lois A. Scheffler, Windham, NH (US); Paula J. Hart, Boxford, MA (US); Alice M. Chiang, Weston, MA (US)

(73) Assignee: TeraTech Corporation, Burlington, MA (US)

( * ) Notice: Subject to any disclaimer, the term of this patent is extended or adjusted under 35 U.S.C. 154(b) by 33 days.

(21) Appl. No.: 09/822,764

(22) Filed: Mar. 30, 2001

(65) Prior Publication Data

US 2002/0067359 A1 Jun. 6, 2002

Related U.S. Application Data

(63) Continuation-in-part of application No. 09/791,491, filed on Feb. 22, 2001, which is a continuation-in-part of application No. PCT/US00/17236, filed on Jun. 22, 2000, which is a continuation-in-part of application No. 09/449,780, filed on Nov. 26, 1999, now Pat. No. 6,530,887.

(60) Provisional application No. 60/140,430, filed on Jun. 22, 1999.

(51) Int. Cl.[7] .................................................. A61B 8/00

(52) U.S. Cl. ..................................................... 600/437

(58) Field of Search ............................... 600/443, 447, 600/437; 345/581, 589, 591, 594, 676, 713, 160–161, 163, 173

(56) References Cited

U.S. PATENT DOCUMENTS

| 4,070,905 A | 1/1978 | Kossoff .................. 73/614 |
| 4,140,022 A | 2/1979 | Maslak .................. 73/626 |
| 4,159,462 A | 6/1979 | Rocha et al. ........... 340/1 |
| 4,310,907 A | 1/1982 | Tachita et al. ......... 367/11 |
| 4,319,489 A | 3/1982 | Yamaguchi et al. .... 73/626 |
| 4,344,327 A | 8/1982 | Yoshikawa et al. .... 73/626 |
| 4,368,643 A | 1/1983 | Tachita et al. ......... 73/626 |
| 4,573,477 A | 3/1986 | Namekawa et al. .... 128/663 |

(List continued on next page.)

FOREIGN PATENT DOCUMENTS

| WO | WO 98/28631 | 7/1998 |
| WO | WO 98/34294 | 8/1998 |
| WO | WO 00/79300 | 12/2000 |

OTHER PUBLICATIONS

Strassberg, Dan, "Despite Threats from USB and Firewire, IEEE 488 ain't down yet," *EDN Electrical Design News* 43(15):67–80 (1998).

Primary Examiner—Francis J. Jaworski
(74) Attorney, Agent, or Firm—Bowditch & Dewey, LLP

(57) ABSTRACT

Conventional ultrasound imaging systems typically include a hand-held probe coupled to a processing and display unit. Typical controls in an ultrasound imaging system require that the operator continually focus on the controls, rather than the ultrasonic image of the area of interest, and manually manipulate the controls by moving their hand along the control panel. By controlling an ultrasonic imaging system from a unitary operating position, defining ultrasonic imaging operations and defining a ranges of values corresponding to each of the ultrasonic imaging operations, ultrasonic image processing is facilitated. An operator selects, via a first control, one of the ultrasonic imaging operations, and then selects, via a second control, a parameter in the range of values corresponding to the selected ultrasonic imaging operation. The ultrasonic imaging system applies the selected ultrasonic imaging operation employing the selected parameter. In this manner, the operator produces the desired ultrasonic image processing results by employing both the first control and the second control from a common operating position from one hand, thereby allowing the operator to continue scanning with a free hand while continuing to control the ultrasonic imaging system.

35 Claims, 19 Drawing Sheets

U.S. PATENT DOCUMENTS

| | | | |
|---|---|---|---|
| 4,582,065 A | 4/1986 | Adams ........................ 128/660 |
| 4,622,977 A | 11/1986 | Namekawa et al. ........ 128/663 |
| 4,664,122 A | 5/1987 | Yano ........................... 128/660 |
| 4,759,375 A | 7/1988 | Namekawa ................. 128/663 |
| 4,852,577 A | 8/1989 | Smith et al. ........... 128/660.07 |
| 4,896,283 A | 1/1990 | Hunt et al. .................. 364/577 |
| 4,937,797 A | 6/1990 | Snyder et al. .............. 367/138 |
| 4,949,259 A | 8/1990 | Hunt et al. ............. 364/413.25 |
| 4,962,667 A | 10/1990 | Ogawa et al. ................. 73/626 |
| 5,123,415 A | 6/1992 | Daigle ................... 128/661.01 |
| 5,148,810 A | 9/1992 | Maslak et al. ......... 128/661.01 |
| 5,235,986 A | 8/1993 | Maslak et al. ......... 128/661.01 |
| 5,261,408 A | 11/1993 | Maslak et al. ......... 128/661.01 |
| 5,295,485 A | 3/1994 | Shinomura et al. .......... 600/443 |
| 5,383,457 A | 1/1995 | Cohen ................... 128/660.07 |
| 5,590,658 A | 1/1997 | Chiang et al. .......... 128/661.01 |
| 5,609,155 A | 3/1997 | Guracar ................ 128/661.09 |
| 5,615,679 A | 4/1997 | Ri et al. ................ 128/660.05 |
| 5,680,536 A | 10/1997 | Tyuluman ................... 395/180 |
| 5,690,114 A | 11/1997 | Chiang et al. ......... 128/661.01 |
| 5,715,823 A | 2/1998 | Wood et al. ............ 600/660.01 |
| 5,722,412 A | 3/1998 | Pflugrath et al. ...... 600/662.03 |
| 5,758,649 A | 6/1998 | Iwashita et al. ....... 128/662.03 |
| 5,763,785 A | 6/1998 | Chiang ........................ 73/609 |
| 5,795,297 A | 8/1998 | Daigle ........................ 600/447 |
| 5,798,461 A | 8/1998 | Banta et al. ................... 73/625 |
| 5,817,024 A | 10/1998 | Ogle et al. .................. 600/447 |
| 5,839,442 A | 11/1998 | Chiang et al. ......... 128/661.01 |
| 5,860,930 A | 1/1999 | Guracar ...................... 600/455 |
| 5,891,030 A * | 4/1999 | Johnson et al. ............. 600/407 |
| 5,893,363 A | 4/1999 | Little et al. .................. 600/447 |
| 5,904,652 A | 5/1999 | Gilbert et al. .............. 600/447 |
| 5,957,846 A | 9/1999 | Chiang et al. .............. 600/447 |
| 5,961,610 A | 10/1999 | Kelly et al. .................. 709/300 |
| 5,964,709 A | 10/1999 | Chiang et al. .............. 600/447 |
| 6,032,120 A | 2/2000 | Rock et al. ..................... 705/2 |
| 6,063,030 A | 5/2000 | Vara et al. ................... 600/437 |
| 6,106,472 A | 8/2000 | Chiang et al. .............. 600/447 |
| 6,111,816 A | 8/2000 | Chiang et al. .................. 367/7 |
| 6,139,498 A | 10/2000 | Katsman et al. ............. 600/443 |
| 6,142,946 A | 11/2000 | Hwang et al. ............... 600/459 |
| 6,198,283 B1 | 3/2001 | Foo et al. .................... 324/309 |
| 6,306,089 B1 * | 10/2001 | Coleman et al. ............. 600/437 |
| 6,337,481 B1 | 1/2002 | Sterns et al. ........... 250/363.03 |
| 6,368,279 B1 * | 4/2002 | Liu ............................. 600/443 |
| 6,379,306 B1 | 4/2002 | Washburn et al. ........... 600/454 |
| 6,381,557 B1 | 4/2002 | Babula et al. ............... 702/183 |
| 6,464,636 B1 * | 10/2002 | Kinicki et al. ............... 600/437 |
| 6,530,887 B1 | 3/2003 | Gilbert et al. ............... 600/459 |

\* cited by examiner

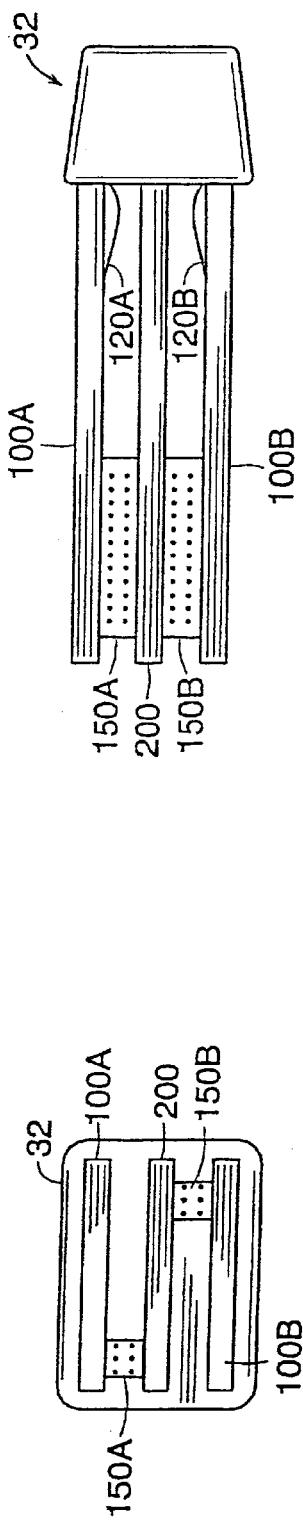
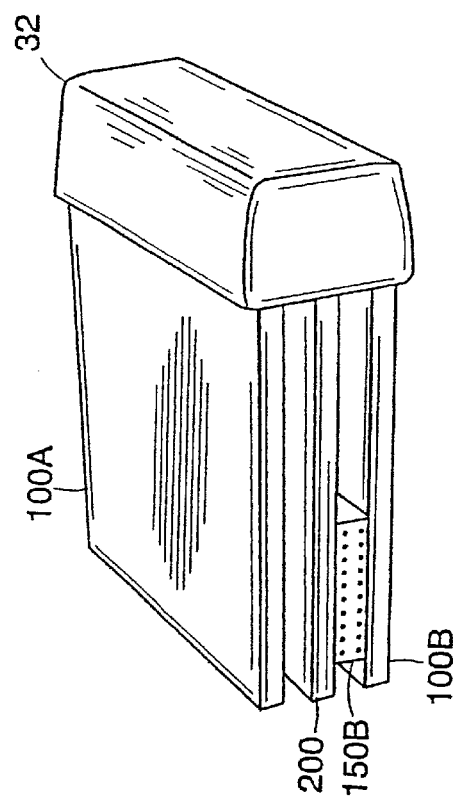

UNITARY OPERATOR CONTROL FOR ULTRASONIC IMAGING GRAPHICAL USER INTERFACE

RELATED APPLICATIONS

This application is a continuation-in-part of application Ser. No. 09/791,491 filed Feb. 22, 2001, which is a continuation-in-part of International Application No. PCT/US00/17236 filed on Jun. 22, 2000, now Publication No. WO00/79300, which is a continuation-in-part of U.S. application Ser. No. 09/449,780 filed on Nov. 26, 1999, now U.S. Pat. No. 6,530,887, issued Mar. 11, 2003, and claims the benefit of U.S. Provisional Application No. 60/140,430, filed on Jun. 22, 1999, the entire contents of the above applications being incorporated herein by reference in their entirety.

BACKGROUND OF THE INVENTION

Conventional ultrasound imaging systems typically include a hand-held probe coupled by cables to a large rack-mounted console processing and display unit. The probe typically includes an array of ultrasonic transducers which transmit ultrasonic energy into a region being examined and receive reflected ultrasonic energy returning from the region. The transducers convert the received ultrasonic energy into low-level electrical signals which are transferred over the cable to the processing unit. The processing unit applies appropriate beam forming techniques to combine the signals from the transducers to generate an image of the region of interest.

Typical conventional ultrasound systems include a transducer array each transducer being associated with its own processing circuitry located in the console processing unit. The processing circuitry typically includes driver circuits which, in the transmit mode, send precisely timed drive pulses to the transducer to initiate transmission of the ultrasonic signal. These transmit timing pulses are forwarded from the console processing unit along the cable to the scan head. In the receive mode, beamforming circuits of the processing circuitry introduce the appropriate delay into each low-level electrical signal from the transducers to dynamically focus the signals such that an accurate image can subsequently be generated.

Typically, the console processing and display unit employs an array of controls, such as knobs, sliders, and switches, which are used to determine the ultrasonic operations to be applied. Such controls require that the operator continually focus on the controls, rather than the ultrasonic image of the area of interest, and manually manipulate the controls by moving their hand along the control panel. Since real-time ultrasonic imaging requires that the hand-held probe be manipulated over the subject area of interest, the operator only has one hand with which to manipulate the controls. Since skillful manipulation of the hand-held probe is required to obtain quality images, it is often the non-dominant hand which must be used to manipulate the controls. Further, since some type of conductive substance, such as gel or paste is often employed on the hand-held probe to facilitate image communication with the subject, continuous, uninterrupted manipulation of the hand-held probe is desirable.

It would be beneficial, therefore, to provide a method of controlling all operations in an ultrasonic imaging system from a common operating position, facilitating selection of qualitative operations and corresponding quantitative parameters with the non-dominant hand, thereby relieving the operator from detracting focus from the subject ultrasonic image, from searching the control panel for unwieldy controls, and from interrupting the ultrasonic scanning to manipulate the controls.

SUMMARY OF THE INVENTION

A method for controlling an ultrasonic imaging system from a unitary operating position facilitates ultrasonic image processing by defining ultrasonic imaging operations and defining a range of values corresponding to each of the ultrasonic imaging operations. An operator then selects, via a first control, one of the ultrasonic imaging operations, and then selects, via a second control, a parameter in the range of values corresponding to the selected ultrasonic imaging operation. The ultrasonic imaging system applies the selected ultrasonic imaging operation employing the selected parameter. In this manner, the operator produces the desired ultrasonic image processing results by employing both the first control and the second control from a common operating position from one hand, thereby allowing the operator to continue scanning with a free hand while continuing to control the ultrasonic imaging system.

The ultrasonic imaging system is controlled from a control keypad accessible from one hand of the operator, or user. The other hand of the operator may therefore be employed in manipulating an ultrasonic probe attached to the ultrasonic imaging system for gathering ultrasonic data employed in the ultrasonic imaging operations. The first control allows qualitative selection of the various ultrasonic imaging operations which may be invoked using the system. The second control allows quantitative selection of parameters along a range to be employed in the ultrasonic operation. The range of parameters may be a continuum, or may be a series of discrete values along the range. The control keypad includes two keys for scrolling through the qualitative ultrasonic operations, and two keys for selecting the quantitative parameters along the corresponding range.

The ultrasonic imaging operations which may be invoked include scanning operations, to be applied to live, real time ultrasonic image gathering, and processing operations, which may be applied to a live or frozen ultrasonic images. Typical scanning ultrasonic imaging operations which are known to those skilled in the art and which may be applied by the ultrasonic imaging system include size, depth, focus, gain, Time Gain Compensation (TGC) and TGC lock. Typical processing ultrasonic imaging operations include view, inversion, palette, smoothing, persistence, map, and contrast.

BRIEF DESCRIPTION OF THE DRAWINGS

FIGS. 2A–2C illustrate a particular embodiment of packaging integrated probe electronics.

Figure 1:
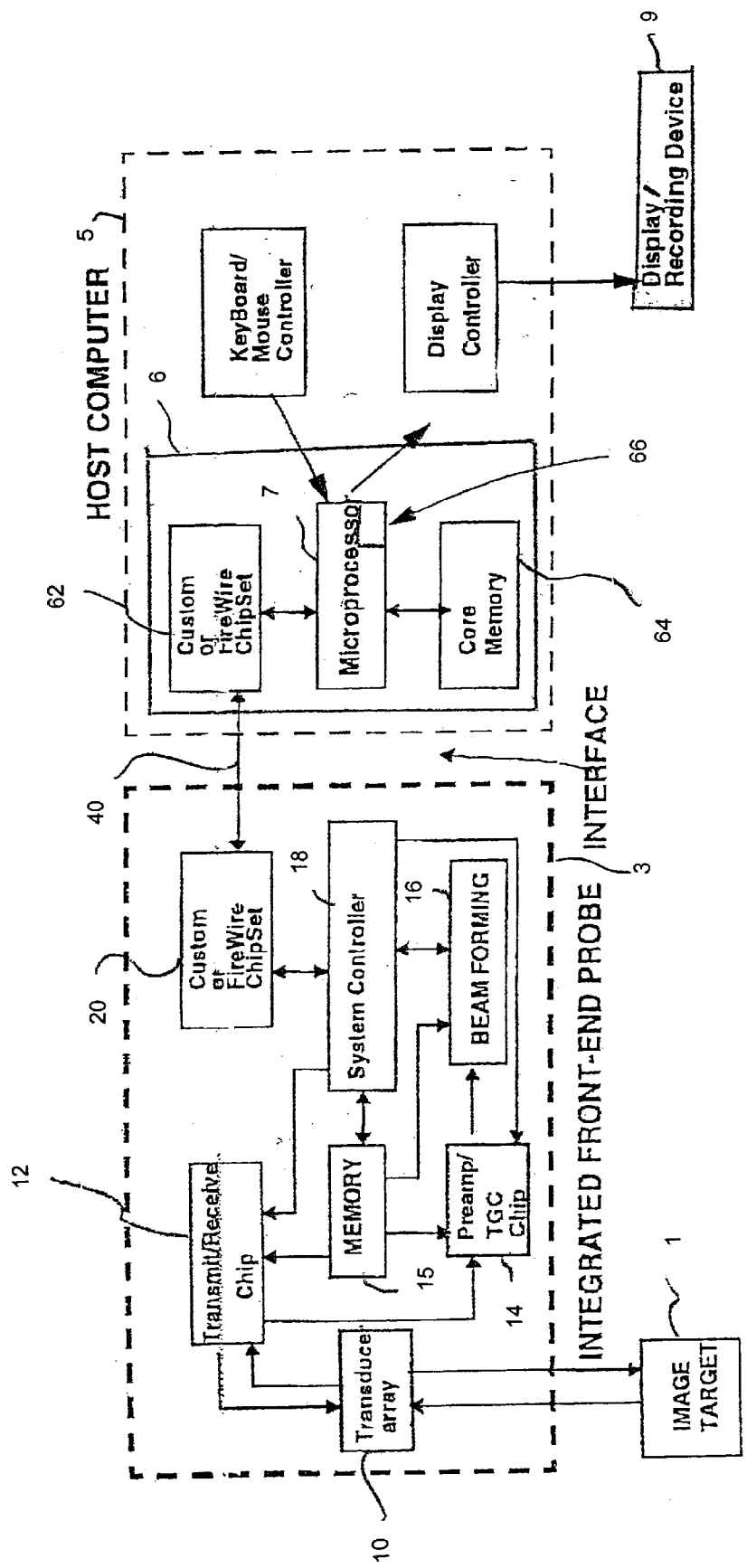
FIG. 1 is a schematic block diagram of an integrated probe system.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

FIG. 1 is a schematic block diagram of an integrated probe system. Illustrated are a target object 1, a front-end probe 3, and a host computer 5. The front-end probe 3 integrates a transducer array 10 and control circuitry into a single hand-held housing. The control circuitry includes a transmit/receive module 12, a pre-amp/TGC module 14, a charge domain processor (CDP) beamforming module 16, and a system controller 18. Memory 15 stores program instructions and data. The CDP beamformer integrated circuit 16 includes a computational capacity that can be used to calculate the delay coefficients used in each channel. The probe 3 interfaces with the host computer 5 over a communications link 40, which can follow a standard high-speed communications protocol, such as the Fire Wire (IEEE 1394 Standards Serial Interface) or fast (e.g., 200 Mbits/second or faster) Universal Serial Bus (USB 2.0) protocol. The standard communication link to the personal computer operates at least at 100 Mbits/second or higher, preferably at 200 Mbits/second, 400 Mbits/second or higher. Alternatively, the link 40 can be a wireless connection such as an infrared (IR) link. The probe 3 thus includes a communications chipset 20.

The components in the portable ultrasound system require a continuous source of data for correct operation. For instance, the beamformer 16 requires steering data, the transmit circuitry 12 requires data to instruct it where to focus the next pulse and when to fire, and the TGC 14 needs to know what gain level is appropriate at the given time. Additionally, further information may be required synchronous to the scanning operation to control how the beamformed data is sent back to the host. For instance, a DATA-VALID signal can be helpful to reduce the amount of data that the host 5 actually has to process. Along with data, the various parts of the ultrasound system relies on common synchronization for the system to work in harmony. For example, the transmitter must be fired at an exact time with respect to when the beamformer is looking at a particular position.

Engineering goals of the ultrasonic probe include small size, thermal management, low-power consumption, and the capability and flexibility to allow efficient high resolution imaging as well as calibration and experimentation. The small size and low-power operation implies dense storage. The capability and flexibility entails the ability to use irregular firing sequences, concurrent reprogramming and use for seamless adaptive beamforming modes, as well as full flexibility to perform debugging and complete-set imaging. Ergonomic, economic portable design also requires a cost-effective, non-encumbering connection between the scan head 3 and the PC host 5. A general description of the probe system can be found in International Application PCT/US96/11166, filed on Jun. 28, 1996, now U.S. Pat. No. 5,964,709 issued on Oct. 12, 1999, which is a continuation-in-part application of U.S. Ser. No. 08/599,816 filed on Feb. 12, 1996, now U.S. Pat. No. 5,690,114, issued on Nov. 25, 1997, which is a continuation-in-part application of U.S. Ser. Nos. 08/496,804 and 08/496,805 both filed on Jun. 29, 1995, now U.S. Pat. Nos. 5,590,658 and 5,839,442, and further embodiments are described in U.S. application Ser. No. 09/364,699 filed July 30, 1999 which corresponds to International Application No. PCT/US98/02291 filed on Feb. 3, 1998, now Publication No. WO98/34294, and in U.S. application Ser. No. 09/447,144 filed on Nov. 23, 1999, now U.S. Pat. No. 6,379,304, issued on Apr. 30, 2002, which corresponds to International Application No. PCT/US97/24291 filed on Dec. 23, 1997, now Publication No. WO98/28631, the above patents and applications being incorporated herein by reference in their entirety.

Additional factors of interest include ease, speed, and low-cost of design and manufacturing. These factors motivate the use of a Field Programmable Gate Array (FPGA) architecture. Additionally, they involve the use of a design that can be extended easily to diverse applications.

FIGS. 2A–2C illustrate a particular embodiment of integrated probe electronics. FIG. 2A is a perspective view showing a transducer array housing 32, an upper circuit board 100A, a lower circuit board 100B, and a central circuit board 200. Also shown is a lower Molex connector 150B carrying data and signal lines between a central circuit board 200 and the lower circuit board 100B. The transducer array housing 32 can be a commercially available unit having a pair of flexible cable connectors 120A, 120B (See FIG. 2C) connected to the upper board 100A and lower board 100B, respectively, with strain relief. FIG. 2B is a back-end view of the probe, which also shows an upper Molex connector 150A. FIG. 2C is a side view of the probe. Using 8 mm high Molex connectors 150A, 150B, the entire stack has a thickness of approximately 30 mm or less, with this particular embodiment being about 21 mm.

Small size is achieved through the use of modern fabrication and packaging techniques. For example, by exploiting modern semiconductor fabrication techniques, numerous circuit functions can be integrated onto single chips. Furthermore, the chips can be mounted using space-saving packaging, such as chip on-board technology. As technology improves, it is expected that the size of the electronic components will decrease further.

More functionality can be included within the handheld probe such as a wireless IEEE 1394 connection to the personal computer. A display can be mounted directly on the handheld probe, for example, to provide a more usable and user-friendly instrument.

Figure 3A:
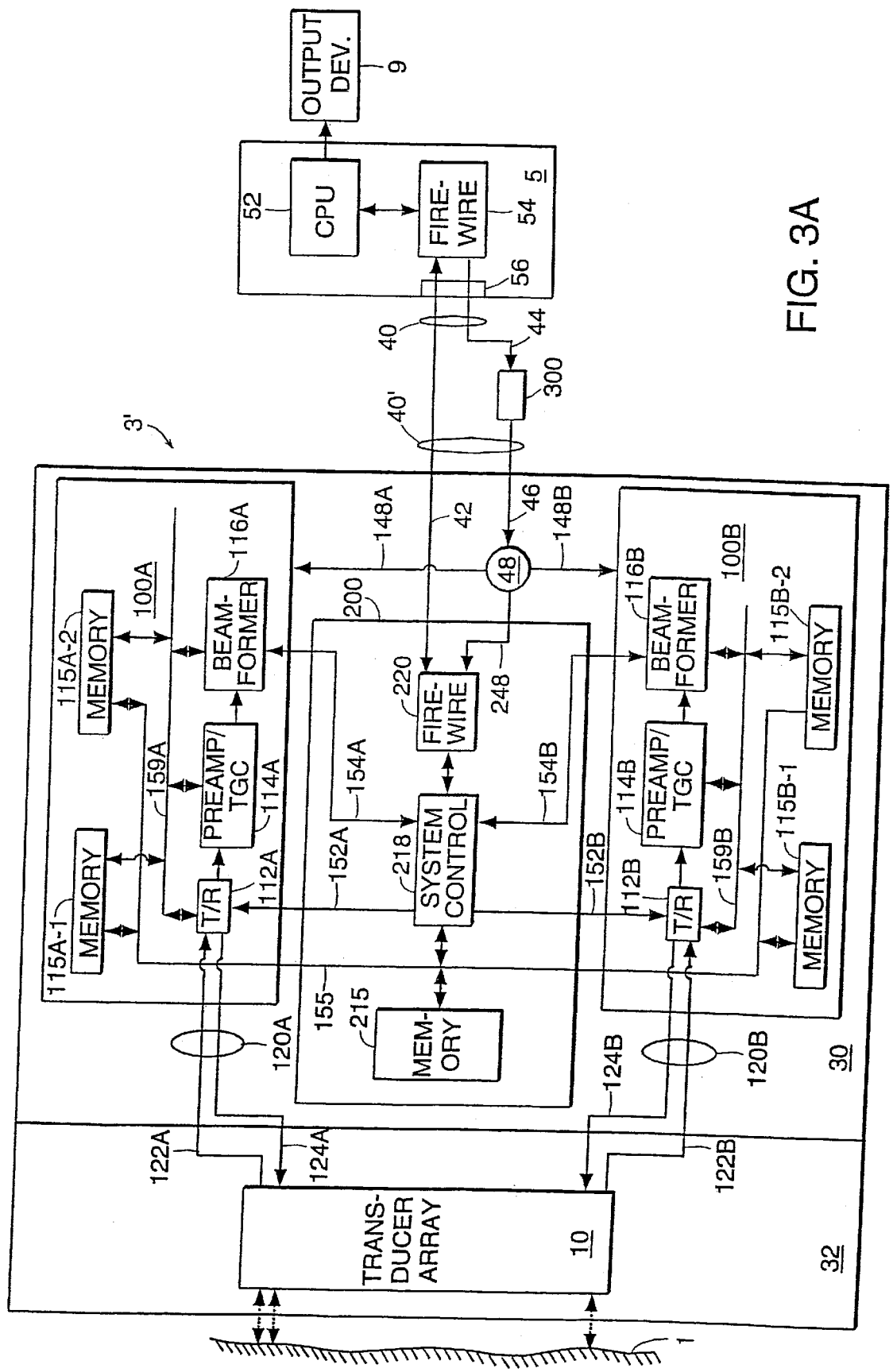
FIG. 3A is a schematic block diagram of a particular embodiment of an integrated probe system.

FIG. 3A is a schematic block diagram of a particular embodiment of an integrated probe system. The host computer 5 can be a commercially available personal computer having a microprocessor CPU 52 and a communications chipset 54. A communications cable 40 is connected through a communications port 56 to the communications chipset 54.

The front-end probe 3' includes a transducer head 32, which can be an off-the-shelf commercial product, and an ergonomic handheld housing 30. The transducer head 32 houses the transducer array 10. The housing 30 provides a thermally and electrically insulated molded plastic handle that houses the beamforming and control circuitry.

The beamforming circuitry, as shown, can be embodied in a pair of analog circuit boards 100A, 100B. Each analog circuit board 100A, 100B includes a respective transmit/receive chip 112A, 112B; a preamp/TGC chip 114A, 114B; a beamformer chip 116A, 116B; all of which are interconnected with a pair of the memory chips 115A-1, 115B-1, 115A-2, 115B-2 via an operational bus 159A, 159B. In a particular embodiment of the invention, the memory chips are Video Random Access Memory (VRAM) chips and the operational bus is 32 bits wide. Furthermore, preamp/TGC chips 114 and beamformer chips 116 operate on 32 channels simultaneously. The transmit/receive chips 112 include a 64 channel driver and a 64-to-32 demultiplexer.

Figure 4A:
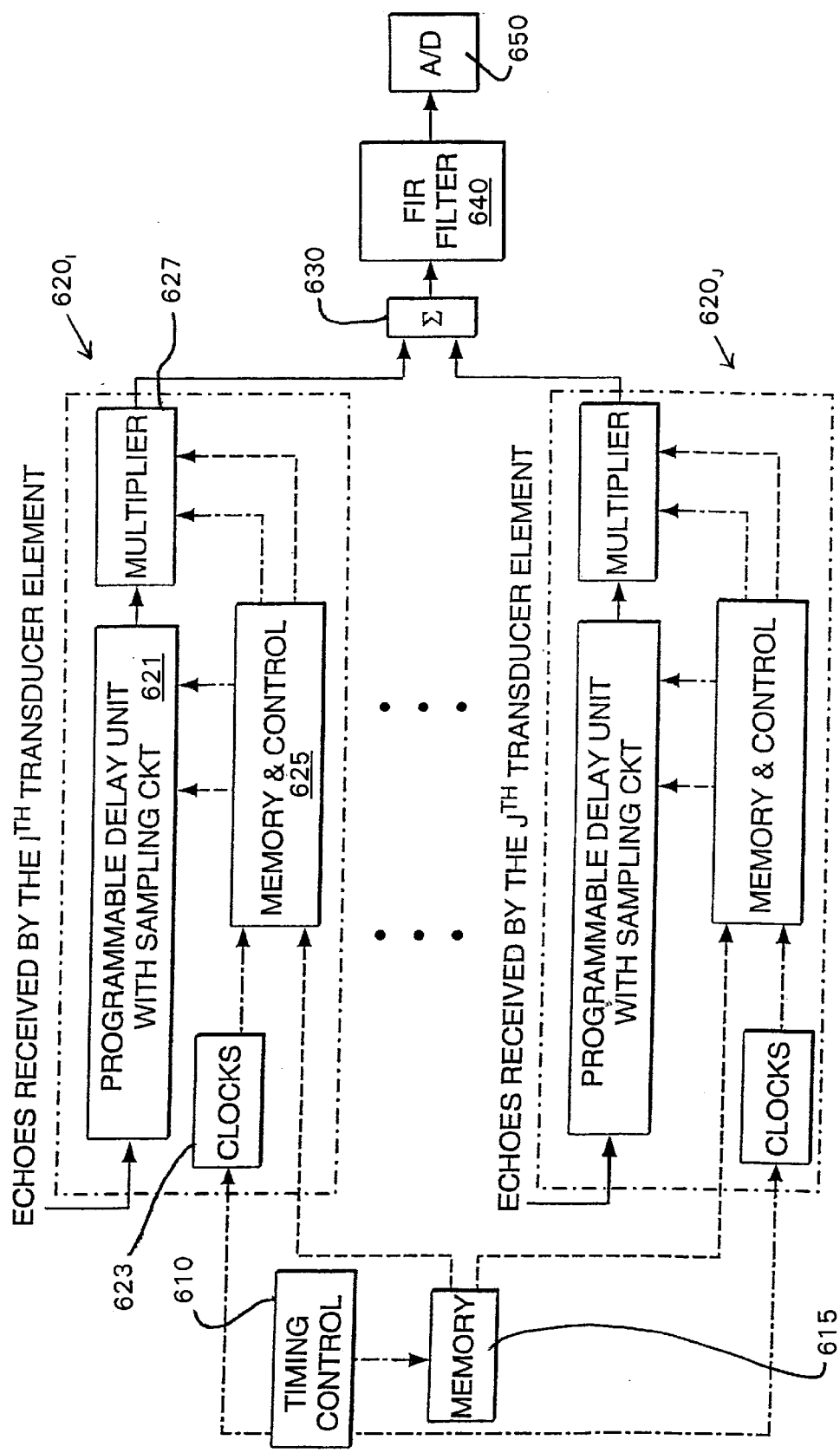
FIG. 4A is a block diagram of a particular 1-dimensional time-domain beamformer.

FIG. 4A is a block diagram of a particular 1-dimensional time-domain beamformer. The beamformer 600 features 32-channel programmable apodized delay lines. In addition, the beamformer 600 can include an on-chip output bandpass filtering and analog-to-digital conversion.

As illustrated in FIG. 4A, the beamformer 600 includes a plurality of single channel beamforming processors 620 subscript I, . . . , 620 subscript J. Imaging signals are represented by solid leader lines, digital data is represented by dashed leader lines, and clock and control signals are illustrated by alternating dot and dash leader lines. A timing controller 610 and memory 615 interface with the single channel beamforming processors 620. Each single channel beamforming processor includes clock circuitry 623, memory and control circuitry 625, a programmable delay unit with sampling circuitry 621, in a multiplier circuit 627.

Each programmable delay unit 621 receives an imaging signal echo E from a respective transducer element. The outputs from the single channel beamforming processors 620 are added in a summer 630. An FIR filter 640 processes the resulting imaging signal, which is digitized by the analog-to-digital (A/D) converter 650. In a particular embodiment of the invention, both the FIR filter 640 and the A/D converter 650 are fabricated on chip with the beamforming processors 620.

The choice of an FPGA implementation as well as extensibility for ease of modification, points to the use of VRAMs for the memory modules. VRAM is a standard Dynamic RAM (DRAM) with an additional higher-speed serial access port. While DRAM has two basic operations e.g. read and write memory location, VRAM adds a third operation: transfer block to serial readout register. This transfers a block (typically 128 or 256 words) of data to the serial readout register which can then be clocked out at a constant rate without further tying up the DRAM core. Thus refresh, random access data read/write, and sequential readout can operate concurrently.

In the probe 3', dual-ported operation is beneficial so the data loading performed by the host 5 can be decoupled from data sent to memory modules. A modular architecture which allows additional VRAMs to be added in order to obtain additional bandwidth is useful, particularly when the exact data rate requirements may change. Using wide memories, the data does not have to be buffered before going to the various destination modules in the system. A particular embodiment uses five 256 K word by 16 bit VRAMs which yields a total of 80 output lines. If fewer output lines are required, fewer VRAMs can be used. If more output lines are required, only very minor modifications to the controller have to be made.

The downside is that VRAM is lower density than other varieties of DRAM. Currently only 512 Kbyte VRAM chips are available. Synchronous DRAM (SDRAM) is a 2 Mbyte/chip, but expects buffering of all data from the memory to the various destination modules because it is not continuous. The use of SDRAM implies that the modules accept data bursts instead of continuous data. Additionally, more buffering of host data can be used or else concurrent readout and loading may not be possible. Using a multiple data rate feature in the controller can reduce the storage requirements making VRAM a first embodiment. However, a further preferred embodiment uses SDRAM to provide further improvements in the speed and capacity of the system.

The control circuitry, as shown in FIG. 3A, is embodied in a digital circuit board 200. The digital circuit board 200 includes a Fire Wire chipset 220, a system control chip 218 to control the scan head, and a memory chip 215. In a particular embodiment of the invention, the memory chip 215 is a VRAM chip and the system control chip 218 is interconnected to the various memory chips 115, 215 over a control bus 155, which in this particular application is 16 bits wide.

As illustrated, the system control chip 218 provides scan head control signals to be transmit/receive chips 112A, 112B over respective signal lines 152A, 152B. The transmit/receive chips 112A, 112B energize the transducer array 10 over transmit lines 124A, 124B. Received energy from the transducer array 10 is provided to the transmit/receive chips 112A, 112B over receive lines 122A, 122B. The received signals are provided to the pre-amp/TGC chips 114A, 114B. After being amplified, the signals are provided to the beamformer chips 116A, 116B. Control signals are exchanged between the beamformer and the system controller over signal lines 154A, 154B to adjust the scan beam.

The five VRAM chips 115A-1, 115A-2, 115B-1, 115B-2, 215 serve to supply the real-time control data needed by the various operating modules. The term "operating modules" refers to the different parts of the system that require control data—namely the beamformers 116A, 116B, transmit/receive chips 112A, 112B, and preamp/TGC chips 114A, 114B. The system controller 218 maintains proper clocking and operation of the VRAM to assure continuous data output. Additionally, it generates clocks and control signals for the various operating modules of the system so that they know when the data present at the DRAM serial port output is for them. Finally, it also interfaces with the host (PC) 5 via a PC communications protocol (e.g., FireWire or high speed bus) to allow the host 5 to write data into the VRAM.

Some of the VRAMs are shared by multiple modules. The 64-bit output of four VRAMs 115A-1, 115A-2, 115B-1, 115B-2 is used by both the transmit module as well as the beamformer. This is not a problem, because typically only one requires data at any given time. Additionally, the transmit module chip uses relatively less data and thus it is wasteful to have to dedicate entire VRAMs for transmit operations. In order to allow the VRAM data to be shared by multiple modules, codes are embedded in the VRAM data that the controller deciphers and asserts the appropriate MODCLOCK line.

The fifth VRAM 215 is used to generate data that is not shared by multiple modules. For example, it is convenient to put the control for the TGC here because that data is required concurrently with beamformer data. It can also be useful to have one dedicated control bit which indicates when valid data is available from the beamformer and another bit indicating frame boundaries. Thus, because the location of the data in the VRAM corresponds to the position in the frame scanning sequence, additional bits are synchronized with the operation of the system. CCD clock enable signals can also be generated to gate the CCD clock to conserve power. Lastly, the VRAM can be used to generate test data for a D/A converter to test the analog circuitry with known waveforms.

As the system is reduced in size, the number of VRAMs may be reduced. In a SDRAM system clocked twice as fast, the four shared VRAM chips may be merged into two SDRAM chips in a 128 line system, for example.

The data sent to the beamformer and transmit modules are bit-serial within a channel, with all channels being available in parallel. For the transmit module, two transmit channels share each bit line with alternating clocks strobing in data for the two channels. All per channel transmit module coefficients (such as start time) are presented bit-serially.

The data in the VRAM is organized into runs. A run consists of a one word header, which is interpreted by the VRAM controller, followed by zero or more actual data words which are used by the various modules. The headers (see Table 1) specify where the data in the run is destined, how fast it should be clocked out, and how many values there are in the run. (Note that the run destination is only for the data coming out of the 4 VRAMs. The bits coming out of the controller VRAM always have the same destination.) The headers are also used to encode the special instructions for Jump, Pause, and End described below.

The data in the VRAM are read out basically sequentially but some variations are allowed to reduce the memory requirements and facilitate system operation based on several observations about how the ultrasound system operates.

The first observation is that the peak control data rate requirements are far higher than the average rates needed. This is because, during close zone imaging, the focus may be updated at every clock to maintain maximal sharpness. However, for deep zones approaching the far field, the focusing parameters need not vary very quickly. Thus the data may be supplied at a lower rate. This is accomplished by the use of a 2-bit RATE field associated with each run (see Table 2). The RATE field allows the specified run to be clocked out at either the full system clock rate (which can be 8–32 MHZ), one-half, one-quarter, or one-eighth of that rate.

TABLE 2

Rate Field Definitions

| Rate | | | |
|---|---|---|---|
| Bit 12 | Bit 11 | Data Meaning | Pause Length |
| 0 | 0 | New Data Every Clock | PauseCount Clocks |
| 0 | 1 | New Data Every Other Clock | PauseCount*2 Clocks |
| 1 | 0 | New Data Every 4 Clocks | PauseCount*4 Clocks |
| 1 | 1 | New Data Every 8 Clocks | PauseCount*8 Clocks |

The next observation is that there are often large gaps during which time data is not required. After a transmit pulse is fired into a deep zone, a relatively large amount of time can pass before its echo is received and the beamformer is activated. Thus it is advantageous to not have to waste VRAM space for work time periods. For this reason, explicit pause commands are allowed. When the system controller 218 receives a pause command, it waits the specified number of clock cycles before reading the next word in the VRAM memory. The PAUSECOUNT is a 11 bit number which can take on the range 1–2047. This is additionally scaled by the RATE field to allow pauses of up to 16376 (2047*8) system clock cycles. Note that the RATE field can only take on the values 0, 2 and 3 because a pause of RATE 1 is interpreted as a wait command, described next. This is not a problem, however, because typically only RATE 0 is used for maximum wait accuracy (to within one clock) and RATE 3 is used for maximum wait time (up to 16376 clock cycles).

Because the data from the beamformer 116 has to be sent back to the host 5 over a bandwidth-constrained link, buffering and flow-control are required to prevent data loss. The buffering is achieved by a 16 K 18 FIFO while the flow control is achieved by feeding the FIFO fullness indication back to the system controller 218. In this way, if the FIFO

TABLE 1

VRAM Instruction Data Format (Only top VRAM matters)

| | Bit Position | | | | | | | | | | | | | | | |
|---|---|---|---|---|---|---|---|---|---|---|---|---|---|---|---|---|
| Command | 15 | 14 | 13 | 12 | 11 | 10 | 9 | 8 | 7 | 6 | 5 | 4 | 3 | 2 | 1 | 0 |
| Data | Mod Sel (2–7) | | | Rate | | | | | | Length | | | | | | |
| Pause | 0 | 0 | 1 | Rate (not 0 1) | | | | | | Pause Count | | | | | | |
| Wait | 0 | 0 | 1 | 0 | 1 | 0 | 0 | 0 | 0 | 0 | 0 | 0 | 0 | 0 | 0 | 1 |
| Jump | 0 | 0 | 0 | 0 | 0 | 0 | Jump Addr / 0x100 | | | | | | | | | |
| End | 0 | 0 | 0 | 0 | 0 | 1 | X | X | X | X | X | X | X | X | X | X | becomes too full, the scanning stops until the FIFO has been emptied. However, the scanning should not stop arbitrarily because it is timed with the propagation of the sound waves. Thus explicit synchronization points can be inserted into the code, and at these points the controller waits until the FIFO is empty enough to proceed safely. The wait command is used to indicate these synchronization points. The wait command causes the controller to wait until the WAITPROCEED line is high. Currently this is connected (via the aux FPGA) to the "not half-full" indicator on the FIFO. Thus the wait commands can be placed at least every 8 K data-generating cycles to assure that data overflow cannot occur. Because this is greater than one ultrasound line, it still allows multi-line interleaving to be used.

The next command is the jump command. This allows non-sequential traversal through the VRAM memory. This is employed so that the VRAM memory can be modified concurrently with the readout operation and also to make it easier to add and remove variable size control sequences. To understand why this is useful, consider the following example: Imagine that one wants to change the data in VRAM locations 512–1023 while continuing operation of the scanning using the other locations. If the host were to just modify locations 512–1023, there is no guarantee that they will not be used exactly when they are in the middle of being modified. Thus the data would be in an indeterminate state and could lead to an erroneous sequence. However, if location 512 is first modified to be a jump to location 1024, and locations to 513–1023 are then modified to their new values, and location 512 is then finally modified to its new value, this race condition cannot occur. (Assuming that it is not reading locations 513–1023 at the start of the modifications but blank regions can be left to get around this.) Additionally "subroutines" (which can only be used once per scan due to the fact that the return is coded as an absolute jump) can be used to allow easy change of the scan sequence.

A jump always takes 128 cycles to execute because the system controller has to load this new start address into the VRAMs and transfer the new row of data to the serial shift register. This typically takes only about 25 cycles, but because other parts of the system controller may have access to the VRAM (such as the refresh or host controller), a safe upper bound is used to maintain a fixed delay.

The last command is the end command. This is used at the end of the sequence for a frame to tell the system controller that the frame has completed. The controller then stops fetching instructions until it is restarted (from location 0) by host if it is in single-frame mode. If it is in continuous mode then it will start immediately on the next frame. (After 128 cycles required for the implied jump 0).

Figure 5A:
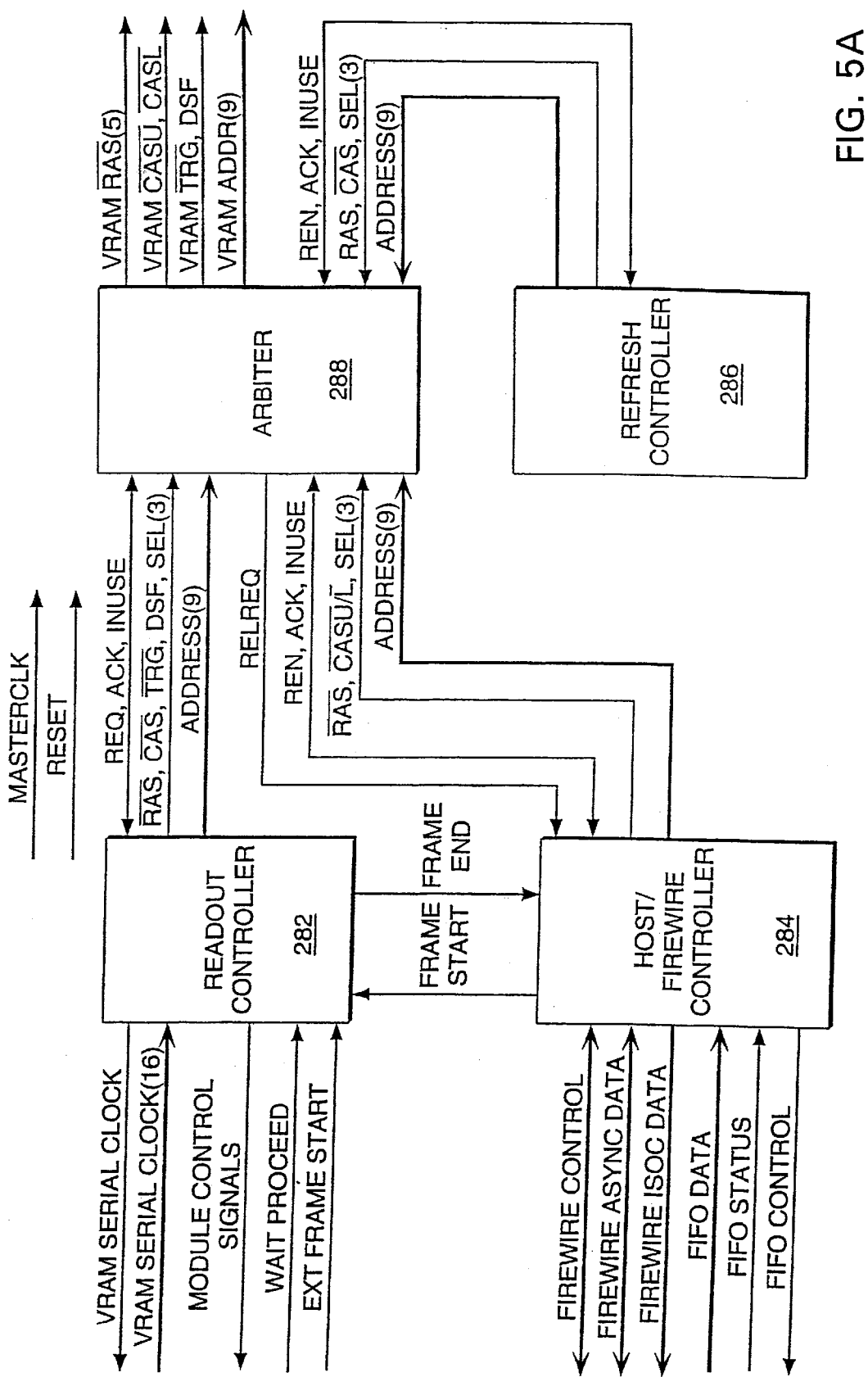
FIG. 5A is a functional block diagram of the system controller of FIG. 3.

FIG. 5A is a functional block diagram of the architecture of the system controller of FIG. 3A. The system controller 218 has four basic parts: a readout controller 282, a host controller 284, the refresh controller 286, and the Arbiter 288. The first three support the three basic operations on the VRAM: reading out data, writing in of data at host's request, and refreshing the DRAM core. The arbiter 288 is responsible for merging the requests of the first three sections into one connection to the VRAM's DRAM core. Only one of the first three sections can have control at a given time, so they explicitly request control and wait until this request is acknowledged by the arbiter 288. They also must tell the arbiter 288 when they are still using the DRAM so that the arbiter knows not to grant it to one of the other sections. This is done via the INUSE lines.

Additionally the arbiter 288 sends the host controller 284 a RELREQ or relinquish request signal to ask the host controller 284 to give up ownership of the DRAM core because some other section wants it. Note that only the host 284 controller needs to be asked to relinquish the bus because the readout controller 284 and refresh controller 286 both only use the DRAM core for fixed short intervals. The host controller 284, however, can hold on to the DRAM as long as there is data coming over the FireWire to be written into the DRAM, so it needs to be told when to temporarily stop transferring data.

Note that the serial section of the VRAMs is not multiplexed—it is always controlled by the readout controller 282. The VRAM serial data also only goes to the readout controller 282.

The readout controller 282 controls the sequencing of the data out the VRAMs' serial access ports. This involves parsing the data headers to determine what locations should be read, clocking the VRAM Serial Clock at the correct time, driving the module control lines, and also arranging for the proper data from the VRAM's DRAM core to be transferred into the serial access memory.

The host controller 284 is the part of the VRAM Controller that interfaces to the host 5 via FireWire to allow the host to write into the VRAM. When the host wants to write into the VRAM, it sends asynchronous packets specifying which VRAM and which addresses to modify as well as the new data to write. The host controller 284 then asks the arbiter 288 for access to the VRAM. When the DRAM core is not in use by either the readout 282 or refresh 286 controller, the arbiter 288 grants control to the host controller 284. The host controller 284 then takes care of address and control signal generation. When the whole packet has been decoded, the host controller 284 releases its request line giving up the DRAM control, allowing the other two sections to use it.

The refresh controller 286 is responsible for periodically generating refresh cycles to keep the DRAM core of the VRAM from losing its data. The refresh controller 286 has its own counter to keep track of when it needs to request a refresh. Once it gains access to the VRAMs via the arbiter 288, it generates one refresh cycle for each of the VRAMs sequentially. This reduces the amount of spikes on the DRAM power supply lines as compared to refreshing all 5 VRAMs in parallel.

The REFRATE inputs control how many system clock cycles occur between refresh cycles. (See Table 3.) This compensates for different system clock rates. Additionally, refresh may be disabled for debugging purposes.

TABLE 3

Refresh Rate Definitions

| RefRate1 | RefRate0 | System clock cycles between refresh cycles | Minimum System Clock to achieve 16 µs refresh rate |
| --- | --- | --- | --- |
| 0 | 0 | 128 | 8 MHZ |
| 0 | 1 | 256 | 16 MHZ |
| 1 | 0 | 512 | 32 MHZ |
| 1 | 1 | No Refresh | ∞ |

The arbiter 288 controls the access to the VRAM by the Readout, Host, and Refresh Controller 282, 284, 286 sections. Only one section may have access to the DRAM port of the VRAM at any given time. The arbiter 288 does not reassign control of the VRAM to another section until the section with control relinquishes it by de-asserting its IN_USE line. The sections are prioritized with the Readout Controller 282 getting the highest priority and the host controller 284 getting the lowest priority. The reasoning is that if the readout controller 282 needs access to the VRAM, but does not get it, then the system may break down as the serial output data will be incorrect. The refresh controller 286 can tolerate occasional delay, although it should not happen much. Finally, the host controller 284 can potentially tolerate very long delays because the host can be kept waiting without too many consequences except that the writing of the VRAM may take longer.

A highly capable, yet cost-effective and physically non-encumbering connection between the scan head and host computer is possible using the FireWire standard (also known as IEEE 1394). The FireWire standard is used for multimedia equipment and allows 100–200 Mbps and preferably in the range of 400–800 Mbps operation over an inexpensive 6 wire cable. Power is also provided on two of the six wires so that the FireWire cable is the only necessary electrical connection to the probe head. A power source such as a battery or IEEE1394 hub can be used. The FireWire protocol provides both isochronous communication for transferring high-rate, low-latency video data as well as asynchronous, reliable communication that can be used for configuration and control of the peripherals as well as obtaining status information from them. Several chipsets are available to interface custom systems to the FireWire bus. Additionally, PCI-to-FireWire chipsets and boards are currently available to complete the other end of the head-to-host connection. CardBus-to-FireWire boards can also be used.

Although the VRAM controller directly controls the ultrasound scan head, higher level control, initialization, and data processing and display comes from a general purpose host such as a desktop PC, laptop, or palmtop computer. The display can include a touchscreen capability. The host writes the VRAM data via the VRAM Controller. This is performed both at initialization as well as whenever any parameters change (such as number or positions of zones, or types of scan head) requiring a different scanning pattern. During routine operation when data is just being continually read from the scan head with the same scanning parameters, the host need not write to the VRAM. Because the VRAM controller also tracks where in the scan pattern it is, it can perform the packetization to mark frame boundaries in the data that goes back to the host. The control of additional functions such as power-down modes and querying of buttons or dial on the head can also be performed via the FireWire connection.

Although FireWire chipsets manage electrical and low-level protocol interface to the FireWire interface, the system controller has to manage the interface to the FireWire chipset as well as handling higher level FireWire protocol issues such as decoding asynchronous packets and keeping frames from spanning isochronous packet boundaries.

Asynchronous data transfer occurs at anytime and is asynchronous with respect to the image data. Asynchronous data transfers take the form of a write or read request from one node to another. The writes and reads are to a specific range of locations in the target node's address space. The address space can be 48 bits. The individual asynchronous packet lengths are limited to 1024 bytes for 200 Mbps operation. Both reads and writes are supported by the system controller. Asynchronous writes are used to allow the host to modify the VRAM data as well as a control word in the controller which can alter the operation mode. Asynchronous reads are used to query a configuration ROM (in the system controller FPGA) and can also be used to query external registers or I/O such as a "pause" button. The configuration ROMs contain a querible "unique ID" which can be used to differentiate the probe heads as well as allow node-lockings of certain software features based on a key.

Using isochronous transfers, a node reserves a specified amount of bandwidth, and it gets guaranteed low-overhead bursts of link access every $\frac{1}{8000}$ second. All image data from the head to the host is sent via isochronous packets. The FireWire protocol allows for some packet-level synchronization and additional synchronization is built into the system controller.

The asynchronous write request packets are sent from the host to the probehead in order to:

a) Configure the Link Layer controller chip (TI GPLynx or TI GP2 Lynx)
b) Control the system controller FPGA
c) Write sequencing data into the VRAM Both the "Asynchronous Write Request with Block Payload" or the "Asynchronous Write Request with Quadlet Payload" forms can be used. The later simply restricts the payload to one quadlet (4 bytes). The formats of the two packets are shown in Table 4 and Table 5. Note that these are how the packets are passed on by the TI LINK controller chip. The difference between this and the format over the wire is that the CRCs are stripped and the speed code (spd) and acknowledgment code (ackSent) are appended to the end. The Adaptec API and device driver take care of assembling the packets.

TABLE 4

Asynchronous Write Request with Quadlet Payload as Delivered by TI LINK chip

Bit (bit 0 is MSB)

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|------|---|---|---|---|---|----|----|----|----|----|----|----|----|----|----|----|----|----|----|----|----|----|----|----|----|----|----|
| 0 | | | | | | | | | | | | tLabel | | | | | rt | | | tCode = 0 | | | | | priority | | |
| 1 | | | | | | | | | | | | | | | | | | destinationOffsetHi | | | | | | | | | |
| 2 | | | | | | | | | | | | | | | | | | | | | | | | | | | |
| 3 | | | | | | | | Data 1 | | | | | | | Data 2 | | | | | | | | Data 3 | | | | |
| 4 | | | | | | | | | | | spd | | | | | | | | | | | | | | | | ackSent |

TABLE 5

Asynchronous Write Request with Block Payload as Delivered by TI LINK chip

Bit (bit 0 is MSB)

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|
| 0 | | | | | | | | | | | | | | tLabel | | | | rt | | tCode = 0 | | | | priority | | | |
| 1 | | | | | | | | | | | | | | | | | | destinationOffsetHi | | | | | | | | | |
| 2 | | | | | | | | | | | | | | | | | | | | | | | | | | | |
| 3 | | | | | | | | | | | | | | | | | | | | extendedTcode | | | | | | | |
| 4 | | | | | | | Data 1 | | | | | | | | | Data 2 | | | | | | | | Data 3 | | | |
| 5 | | | | | | | Data 5 | | | | | | | | | Data 6 | | | | | | | | Data 7 | | | |
| ... | | | | | | | ... | | | | | | | | | ... | | | | | | | | ... | | | |
| 3 + N/4 | | | | | | | Data N-3 | | | | | | | | | Data N-2 | | | | | | | | Data N-1 | | | |
| 4 | | | | | | | | | spd | | | | | | | | | | | | | | | ackSent | | | |

The destinationID field holds the node ID of the destination which is the probe head FireWire controller. The physical layer chip can use this to determine if the packet is for it. The system controller can ignore this field. The tLabel field is used to match requests and responses. For write requests, this does not matter and can be ignored. The rt is the retry code used at link and/or phy level. It is not used by the system controller. The tCode field is the transaction code which determines what type of packet it is. In particular 0 is for quadlet write requests and 1 is for block write requests. The system controller parses this field to determine what type of packet it is. Currently only tCode values of 0 and 1 are recognized. The priority field is used by the PHY chip only and is ignored by the system controller. It is used in, i.e. in selecting which unit on the interface is to receive a particular packet of data.

Next, the destinationOffsetHi and destinationOffsetLo fields form the 48 but destination start address. This indicates within the node what the data should be used for. The system controller used the destinationOffsetHi to determine the function as shown in Table 6. Note that only the 3 least significant bits of the destinationOffsetHi field are currently examined. The spd field indicates the speed at which the data was sent while the ackSent field is use to indicate status by saying how the LINK chip acknowledged the packet.

TABLE 6 destinationOffsetHi values

| destinationOffsetHi | Meaning |
|---|---|
| 0 | Write VRAM 0 |
| 1 | Write VRAM 1 |
| 2 | Write VRAM 2 |
| 3 | Write VRAM 3 |
| 4 | Write VRAM 4 |
| 5 | Write ISO Packet Length Register |
| 6 | Write System Controller Mode Word |
| 7 | Wrote to LINK chip |

As can be seen, destinationOffsetHi values of 0–4 correspond to writing the VRAMs. In this case the destinationOffsetLow is set to the byte address to start writing. This is twice the standard VRAM address which is typically formed in 16-bit words. Note also that the start address (destinationOffsetLow) and the length (dataLength) can both be multiples of 4 such that all operations are quadlet aligned. The payload data is little endian and thus need not be converted if written by an Intel PC host. The length (dataLength) must additionally be between 4 and 128 bytes due to the size of the GPLynx FIFO. The total FIFO size is 200 bytes, but 72 bytes are dedicated to the asynchronous transmit FIFO required for read responses.

A destinationOffsetHi value of 5 signifies that the system controller ISO Packet Length register is to be written. The ISO Packet Length has to be set in the controller to allow it to correctly format the ISO packets back to the host via firewire. An explicit counter in the system controller is used due to the fact that the TI GPLynx chip does not assert the end-of-packet indication until one word too late. Note that the ISO Packet length also has to be set in the LINK chip. The value written is the number of 16-bit words in the ISO Packet length which also has to be set in the LINK chip. The value written is the number of 16-bit words in the ISO packet (i.e. bytes/2) and it is written in little endian order because it is only interpreted by system controller and not the LINK chip.

Specifying a destinationOffsetHi value of 6 signifies that the system controller mode word is to be modified. Currently only the least significant 16 bits are used out of each quadlet and all quadlets go to the same place so writing multiple values just causes the system controller mode word to be rewritten. Please note that the payload data is again little endian. (Putting these two facts together yields that the first two out of every four bytes are used and the second two are ignored.) The definition of the system controller Mode Word is given in Table 7.

TABLE 7

System Controller Mode Word
Bit (bit 31 is MSB)

| 31–36 | 15–8 | 7 | 6 | 5 | 4 | 3 | 2 | 1 | 0 |
|---|---|---|---|---|---|---|---|---|---|
| unused | BOF Word | unused | unused | Abort Frame | Single Frame | Run | Extra2 | Extra1 | Data Loopback |

The BOF Word field is used to set the value that the system controller will put in the high byte of the first word of an isochronous packet to indicate the beginning of frame. The BOF word field can be set to some value that is not likely to occur in typical data. This not crucial, however, because choosing a BOF word that occurs in the data will make it more likely to miss incorrect frame synchronization but will never cause false alarms where it thinks it is mis-synchronized but is really correctly synchronized. The initial value upon reset is 80 hex.

The AbortFrame, SingleFrame, and Run bits are used to control the system operation. Their use is shown in Table 8. The data FIFO is never allowed to fully empty so an entire frame can not be read out until part of the next one is the queue.

TABLE 8

Use of AbortFrame, SingleFrame, and Run bits in System Controller Mode Word

| Abort Frame | Single Frame | Run | Meaning |
|---|---|---|---|
| 1 | 0 | 0 | Abort any current frame and wait |
| 0 | 1 | 0 | Start a single new frame |
| 0 | 0 | 1 | Keep scanning new frames |
| 0 | 0 | 0 | Let any current frame complete |

The DataLoopback bit is used to control whether the data that is read back from the host comes from A/D or from one of the VRAMs. (Currently this is VRAM 1.) This second option can used for test purposes to test the digital data generation and collection without testing the beamformer and A/D conversion. A 0 in the DataLoopback bit indicates normal operation of reading from A/D while a 1 means that it should get data from the VRAM.

The Extra1 and Extra2 bits are available for general use. They are latched by the system controller and currently brought out on pins called EXTRACLOCK0 and EXTRACLOCK1 but can be used for any purpose.

Finally setting destinationOffsetHi to 7 indicates that the data in the asynchronous packet be written back to the FireWire Link chip. This allows any of the TI TSB12LV31's (or 32's) registers to be modified by the host. This can be used to configure and enable the Isochronous data transmit. The destinationOffsetLow specifies the first register to write. Because the registers are all 4-bytes in size and must be written in their entirety, destinationOffsetLow and dataLength must both be multiples of 4. Multiple consecutive registers can be written with a single packet. Note that the data is big-endian because the TSB12LV31 is designed as big-endian. This byte-swapping must be performed by the Intel PC host.

Read request packets are used to asynchronously read data from the probehead. This currently only consists of configuration ROM data (see below) but can be easily used for other types of data such as status information or button indications.

The Adaptec device drivers send Asynchronous Read Requests in response to explicit application requests as well as to interrogate the node's FireWire configuration ROM in response to a SendPAPICommand of P_GET_DEV_INFO or after a bus reset or when an application tries to obtain a handle to a node.

Asynchronous read requests can either be of the quadlet or block variety as with the asynchronous write requests. The formats are shown in Table 9 and Table 10. They are similar to the write request formats.

TABLE 9

Asynchronous Write Request with Quadlet Payload as Delivered by TI LINK chip

Bit (bit 0 is MSB)

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|
| 0 | | | | | | | | | | | | | tLabel | | | | | rt | | tCode = 4 | | | | priority | | | |
| 1 | | | | | | | | | | | | | | | destinationOffsetHi | | | | | | | | | | | | |
| 2 | | | | | | | | | | | | | | | | | | | | | | | | | | | |
| 3 | | | | | | | | | | spd | | | | | | | | | | | | | | ackSent | | | |

TABLE 10

Asynchronous Read Request with Quadlet Payload as Delivered by TI LINK chip

Bit (bit 0 is MSB)

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|
| 0 | | | | | | | | | | tLabel | | | | | | | | rt | | tCode = 5 | | | | priority | | | |
| 1 | | | | | | | | | | | | | | | | destinationOffsetHi | | | | | | | | | | | |
| 2 | | | | | | | | | | | | | | | | | | | | | | | | | | | |
| 3 | | | | | | | | | | | | | | | | | | extendedTcode | | | | | | | | | |
| 4 | | | | | | | | | spd | | | | | | | | | | | | | | | | ackSent | | |

As with the asynchronous write packets, the destinationOffsetHi and destinationOffsetLow determine what is being requested. The high addresses are defined for use as Control and Status Registers and the configuration ROM while the lower address are for more general purpose use. In particular, the FireWire configuration ROM starts at destinationOffsetHi=0xffff, and destinationOffsetLow= 0xf0000400, for example.

When the system controller receives a Quadlet or Block Read Request packet from the TI LINK chip's General Receive FIFO, it formulates a Quadlet or Block Read Response packet and places it in the LINK chip's Asynchronous Transmit FIFO. The format of these packets (as placed in the Asynchronous Transmit FIFO) is shown in Table 11 and Table 12.

The rCode field is used to indicate the status of the reply. In particular, 0 means resp_complete indicating all is well. A value of 6 means resp_type_error indicating that some field of the packet was invalid or unsupported. In this case, if the request was a block request then the dataLength of the response packet must be 0 and no data should be included. A resp_type_error is returned if the dataLength or destinationOffsetLow of the request packet were not multiples of 4 or if the dataLength was not between 4 and 32 (for block packets). This is because the TI chip's asynchronous transmit FIFO is configured to be 12 quadlets (for 8 payload quadlets+4 quadlet header) so that the receive FIFO can be 36 quadlets in order to allow 128 byte payload write packets. The longest request the Adaptec device drivers should request is 8 quadlets because that is the length of the

TABLE 11

Asynchronous Read Request with Quadlet Payload as Expected by TI LINK chip

Bit (bit 0 is MSB)

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|
| 0 | | | | | | | spd | | | | | tLabel | | | | | | rt | | tCode = 6 | | | | priority | | | |
| 1d | | | | | | | | | | | | rCode | | | | | | | | reserved = 0 | | | | | | | |
| 2 | | | | | | | | | | | | | | | | | | | | | | | | | | | |
| 3 | | | | | | | Data 1 | | | | | | | | Data 2 | | | | | | | | Data 3 | | | | |

TABLE 12

Asynchronous Read Response with Block Payload as Expected by TI LINK chip

Bit (bit 0 is MSB)

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|
| 0 | | | | | | | spd | | | | | tLabel | | | | | | rt | | tCode = 7 | | | | priority | | | |
| 1 | | | | | | | | | | | | rCode | | | | | | | | reserved = 0 | | | | | | | |
| 2 | | | | | | | | | | | | | | | | | | | | | | | | | | | |
| 3 | | | | | | | | | | | | | | | | extendedTcode = 0 | | | | | | | | | | | |
| 4 | | | | | | | Data 1 | | | | | | | | Data 2 | | | | | | | | Data 3 | | | | |
| 5 | | | | | | | Data 5 | | | | | | | | Data 6 | | | | | | | | Data 7 | | | | |
| ... | | | | | | | ... | | | | | | | | ... | | | | | | | | ... | | | | |
| 3 + N/4 | | | | | | | Data N-3 | | | | | | | | Data N-2 | | | | | | | | Data N-1 | | | | |

The spd, tLabel, rt, and priority values are copied from the request packet. The destinationID is taken from the sourceID of the request packet. Note that all packet CRCs are generated by the TI LINK chip and are thus note included the data that the system controller must generate. (The ROM CRCs do have to be computed explicitly off-line.)

configuration ROM. In any case, it is assumed that if a long transfer failed, it falls back to a smaller request.

The FireWire specification expects each FireWire node to have a configuration ROM that contains various details about the device, its requirements, and its capabilities. This ROM is to be queried via Read Request packets. There are two types of ROM implementations: a minimal ROM and a general ROM. The former has only one quadlet (4-byte) piece of data indicating a 24-bit vendor ID. The general ROM has many other fields, and many which are optional ranging from the ASCII name of the vendor and device to its power consumption and how to access its capabilities.

One of the required fields in a general ROM is a node unique ID. This consists of the 24-bit vendor ID and a 40-bit chip ID. The 40-bit chip-ID is up to the vendor to assign such that all nodes have unique values. The node unique ID's are required to keep a consistent handle on the device if the FireWire bus is reset or reconfigured during operation. When a device is first opened, the application reads its configuration ROM and determines if it wants to work with it. If so it records its node unique ID and opens a connection to the device via that node unique ID. This is then at any given time mapped to its FireWire ID (16-bit) by the host adapter and its device driver. If the topology changes or a FireWire bus reset occurs, the node's FireWire ID can change, however the node unique ID will not. Thus, in such an event, the adapter automatically determines the new FireWire ID and continues. Thus for smooth operation, particularly with multiple heads attached to the system, implementing node unique iDs and the configuration ROM is required.

The configuration ROM is divided into several sections. The sections of particular interest are the first word, which defines the length and CRC of the ROM, the next 4 words comprising the Bus_Info_Block, which gives some fixed 1394-specific information (such as Node Unique ID), and the last 3 words representing the Root Directory which is a set of key-value tagged entries. Only the two required key-value pairs are included the ROM built into the FPGA. An 8-word ROM that can be used is shown in Table 13.

limited to $\frac{1}{8000}$ second, this is a frame of data. The FireWire specification describes the use of synchronization bits which can be used to tag each isochronous packet with a 4 bit SYNC code. The Adaptec FireWire-to-PCI bridge can then use the Sync field to assure proper frame alignment. However, the TI GPLynx Controller chip only supports frame-level granularity of when to send packets and not packet level so when the System Controller tells the FireWire link chip it has data, it must be prepared to send a whole frame of data. Because the FIFO is much smaller than a frame, a sage option is to reduce the effective FireWire frame size to one packet. Then a specific Beginning of Frame (BOF) code in the high byte of the first word of every ultrasound frame and force the start of ultrasound frames to occur at the beginning of FireWire frames (and packets) and do frame-level synchronization in the Ultrasound application software. For efficiency, a full ultrasound frame of data can still be read in one FireWire call (and hence one interrupt).

There are three steps in setting up for Isochronous head-to-host data transfers. These initialization steps need only be performed once per probe initialization.

The first step is to reserve isochronous bandwidth. This reservation causes a central record of the request (in the FireWire isochronous cycle manager node) to be kept to assure that the total bandwidth allocated does not exceed the total bandwidth of the link. For example, this reservation is achieved using the Adaptec API BusConfig 0 command with Cmd field set to P_ALLOCATE_RESOURCE. A requested payload in bytes is passed in. This can be the amount of data desired in every $\frac{1}{8000}$ second. Setting this value too high simply wastes reserved bandwidth on the FireWire interface which is not a problem if there is only one device. Setting this value too low may constrain the head-to-host data rate.

TABLE 13

FireWire Configuration ROM built into FPGA

Bit (bit 0 is MSB)

| Word | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|---|---|---|---|---|---|---|---|---|---|
| 0 | | | | | | crc_length = 0x07 | | | | | | | | | | | rom_crc_value = 0xfbc8 | | | | | | | | | | |
| 1 | | | | | | 0x33("3") | | | | | | | | 0x39("9") | | | | | | | | | 0x34("4") | | | | |
| 2 | | | | | | cyc_clk_acc = 0xff | | | | | | | max_rec = 6 | | | | | | | | reserve = 0x000 | | | | | | |
| 3 | | | | | | | | | | | | | | | | | | | | | | | | | chip_is_hi = 0 | | |
| 4 | | | | | | | | | | | | | | | | | | | | | | | | | | | |
| 5 | | | | | | | | | | | | | | | | | Root_Dir_CRC = 0xbc8e | | | | | | | | | | |
| 6 | | | | | | | | | | | | module_vendor_id = 1234567(0x12d687) | | | | | | | | | | | | | | | |
| 7 | | | | | | | | | | | | node_capabilities = 0x000000 | | | | | | | | | | | | | | | |

Isochronous packets are used for the probehead-to-host communication of beamformed data. This is conceptually a stream of 16-bit numbers punctuated by frame markers. The frame markers are important to keep in sync with where in the frame the data corresponds. While some ultrasound systems use elaborate frame and line markers embedded in the data, the integrated system can use a single auxiliary bit, which is not sent as part of the data, to mark frame boundaries. Line boundaries can be derived by knowing the VRAM sequencing program.

While asynchronous packets can be sent at will and do not have any guarantee of bandwidth availability, isochronous packets can be used as low-overhead way to send a guaranteed rate of data. Once a peripheral reserves a specified amount of bandwidth, it gets guaranteed bursts of link access every $\frac{1}{8000}$ second. All data from the head to the host is sent via isochronous packets. Because isochronous packets are No overflows or data loss are likely to occur, the scanning may simply proceed slower. The resource allocation call will return both an isochronous channel number as well as the payload size granted. This payload size granted may be less than that requested if part of the link has already been reserved.

The next step is to set the system controller ISO packet length word to tell how long of an ISO packet to expect.

The final step is to initialize the probehead LINK chip. This is done via the writeback to LINK chip asynchronous packets described above. In particular, initializing registers 54h, 58h, and 5ch is necessary. The probehead can then be told to start sequencing and the data will flow back.

If multiple probes are connected to the system then the isochronous bandwidth reservation can take place once but at any given time, only one probe's isochronous transmission (as well as its sequencing) is enabled.

As previously described, isochronous data transfers are used to deliver the probe head data to the host. Maintaining frame synchronization is necessary. The FireWire will support sub-frame packetization of about 3000 bytes but it is up to the system controller to implement frame synchronization on top of this. Synchronization is achieved via two methods:

1. The high byte of the first word in the first packet of a frame is set to the Beginning of Frame (BOF) code. (This can be set in the system controller Mode word).
2. All frames are padded to consume a whole number of packets.

When these two are combined, they guarantee that frame synchronization will be maintained if the correct number of packets are read at a time and the resynchronization can be effected by just scanning the high-byte of the first word of each packet in the data stream.

An example packetization is shown in Table 14. This depicts 4 packets of 4 words (8 bytes) apiece showing one complete ultrasound frame and the first packet of the next frame. The ultrasound frame size is 10 words. As can be seen, the Hi byte of the first word is set to the BOF code. This can be examined to assure that proper synchronization has been maintained. The data is then split into the three packets 1–3. Because the frame ends in the middle of packet 3, the end of packet 3 is padded with the BOF code in the high word. Importantly, this means that the first word of the fourth packet will be the first word of the second frame even though the ultrasound frame size is not a multiple of the packet size.

TABLE 14

Example Packetization of Isochronous Head-to-Host Data

| Packet | Word | Lo Byte | Hi Byte |
|---|---|---|---|
| 1 | 1 | Data 1 Lo | BOF |
| (Frame 1) | 2 | Data 2 Lo | Data 2 Hi |
| | 3 | Data 3 Lo | Data 3 Hi |
| | 4 | Data 4 Lo | Data 4 Hi |
| 2 | 1 | Data 5 Lo | Data 5 Hi |
| (Frame 1) | 2 | Data 6 Lo | Data 6 Hi |
| | 3 | Data 7 Lo | Data 7 Hi |
| | 4 | Data 8 Lo | Data 8 Hi |
| 3 | 1 | Data 9 Lo | Data 9 Hi |
| (Frame 1) | 2 | Data 10 Lo | Data 10 Hi |
| | 3 | Data 1 Lo | BOF |
| | 4 | Data 1 Lo | BOF |
| 4 | 1 | Data 1 Lo | BOF |
| (Frame 2) | 2 | Data 2 Lo | Data 2 Hi |
| | 3 | Data 3 Lo | Data 3 Hi |
| | 4 | . . . | . . . |

The TSB12LV31 (or 32) performs packetization of the isochronous data but informs the system controller of packet boundaries via the ISORST signal. The system controller then uses this to reset its internal word-to-byte multiplexer as well as packetization circuitry. If it receives a frame marker from the FIFO then stops clocking data out of the FIFO until it receive a ISORST pulse.

The module interface defines how the various modules in the system are controlled by the VRAM controller. There are two types of modules, those that receive data from the four VRAMs which are shared (two on each analog board), and those that receive data from the VRAM on the digital board, (via the VRAM controller) which is dedicated. The two types of modules use different control signals to synchronize their operation.

Figure 5B:
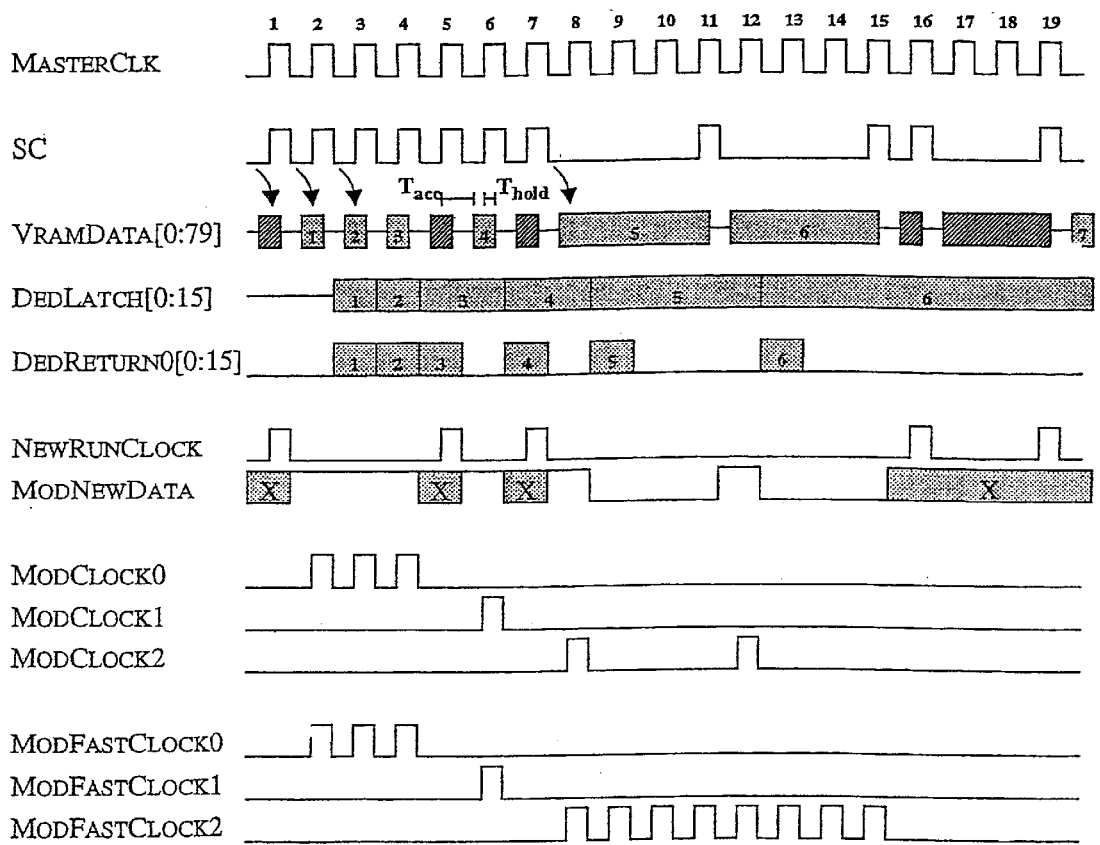
FIG. 5B schematically illustrates a timing diagram for the control of modules in the system.

Much of the timing depends on the speed of the runs of the module (shared/dedicated VRAM usage.) FIG. 5B shows typical timing for the different module interfacing modes for a typical program sequence.

As previously stated, VRAMDATA, the data from the loopback VRAM, control the execution. The diagonal shaded boxes denote header data used by the VRAM controller while the shaded boxes denote module data in FIG. 5B. The data in the four other VRAMs go to the modules. The data from the first VRAM is looped back into the system controller and then used for dedicated data supply for things like the TGC, feedback control, etc.

In clocks 1–4 in FIG. 5B a run of data at a rate 1/1 destined for module 0. The header is clocked out at clock 1. The pulse of NEWRUNCLOCK at clock 1 lets the modules know that the next clock will be the first in a run. They thus reset their internal run-related state if necessary. The data is clocked out during clocks 2, 3, and 4. Since the data is destined for module 0, the MODCLOCK0 is pulsed once per new data word. Module 0 should latch the data at VRAMDATA on the rising edge of MODCLOCK0.

Note that the access and hold times of the VRAM ($T_{acc}$ and $T_{hold}$ in FIG. 5B) must be observed carefully. Since the access time of the VRAM is 15 ns–25 ns depending on the speed grade the hold time can be as low as 4 ns, this does not leave a lot of margin when operating at data no earlier than $T_{clk}-T_{acc}$ before the rising edge of their module clock. (Any skew between SC and the MODCLOCK tightens this bound accordingly but due to the way the VRAM controller was designed to generate both signals as gated clocks from the same MASTERCLK the skew is minimal assuming that the loading conditions are not too dissimilar.) Given a master clock frequency of 33 MHz and the fast VRAM, this gives 15 ns slack. Using the slower VRAMs gives 5 ns slack.

The modules accepting data at the full rate must additionally make sure that they do not latch the data more than $T_{hold}$ after the rising clock. This is because the same clock is used to retrieve the next words from the VRAM. Thus in general modules should make sure to delay the data inputs at least as much as they delay the clock inputs to effectively clock at or before the rising edge of their module clock. This second constraint does not exist when 1/2, 1/4, or 1/8 rate data is used.

Since the first example is of 1/1 rate data, the MODULEFASTCLOCK0 signal follows the MODULECLOCK0 line. They will only differ when 1/2, 1/4, or 1/8 rate data is used.

Clocks 7–15 show a run of length 2 at rate 1/4 destined for Module 2. Thus new data will be clocked out of the VRAMs only once every $4^{th}$ master clock. Here MODULEFASTCLOCK2 will exhibit different behavior than MODULECLOCK2. Again the NEWRUNCLOCK at clock 7 signals that a new run is beginning on the next clock cycle. During clock 7, the VRAM controller has latched the header data indicating that the next run is for module 2 at a rate of 1/4. Also during clock 7, the VRAM generates the module data that the module will use. At clock 8, a MODCLOCK2 occurs, telling module 2 to latch in and use the VRAM's data. Note that the data will present until the master clock before the next MODCLOCK2.

Although MODCLOCK2 is only clocked once per new data word, MODULEFASTCLOCK2 is clocked once per master clock for the duration of the run. This is useful for modules, such as the beamformer which may only need data at a lower rate but need to perform computation at the full rate. The MODNEWDATA signal can also be used by modules using the MODFASTCLOCK lines to determine on which of the fast clocks new data has been presented.

Clocks 16–18 show the result of a pause command. Here the NEWRUNCLOCK is sequenced as usual but no MODCLOCK or MODFASTCLOCK is generated.

Figure 4B:
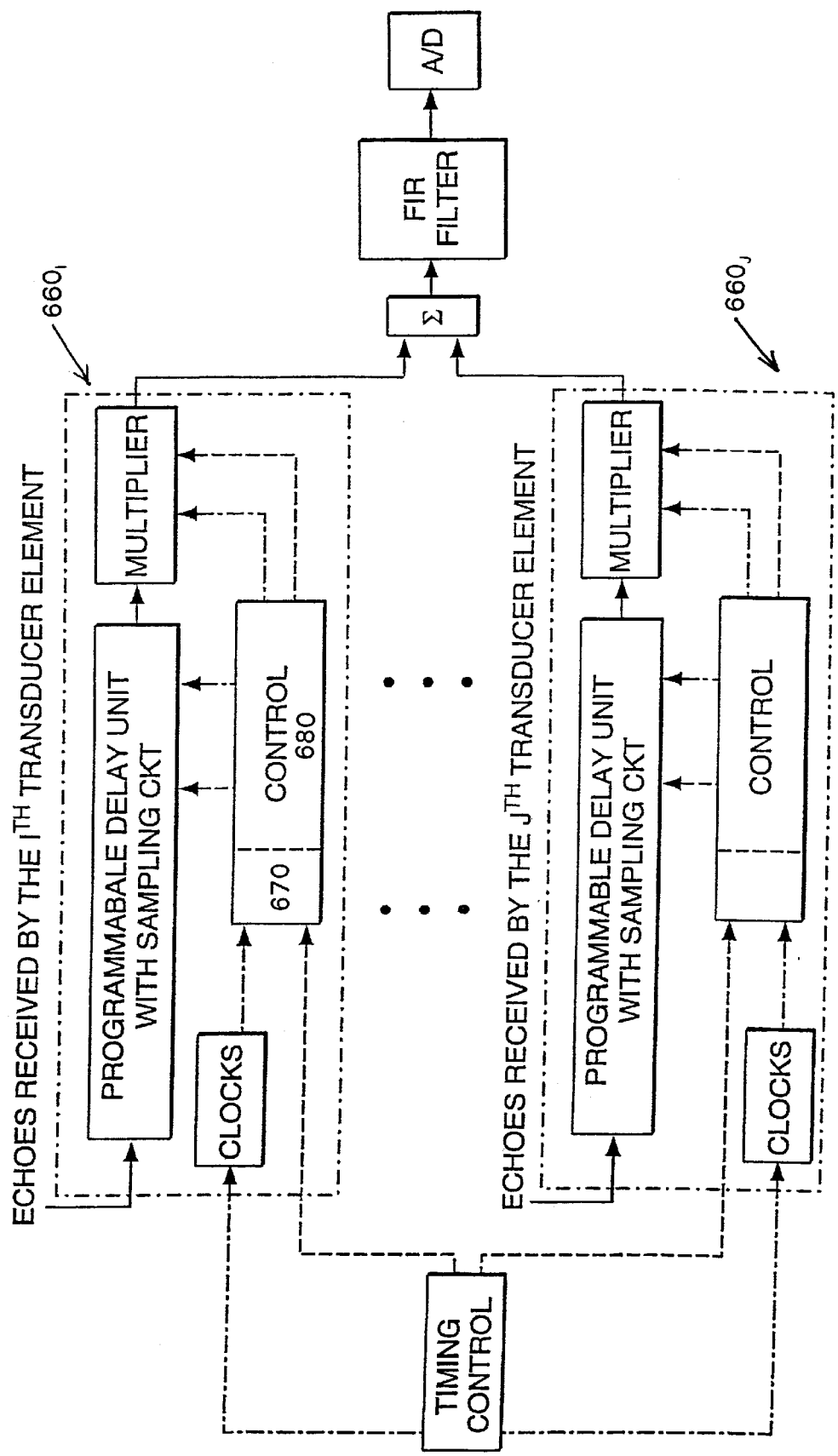
FIG. 4B illustrates another preferred embodiment of a beamformer in accordance with the invention.

As noted above, the particular embodiment was chosen based on a number of criteria, including simplicity of implementation using an FPGA. This motivated the use of VRAMs. An ASIC interface using more dense SDRAM requires at least some buffering, but this can be built into the controller, or alternatively, with the beamformer, T/R circuit or amplifier modules. In this way they receive bursts of data as opposed to the simple synchronous, continuous data that the above system supplies. The benefit is that SDRAMs are more dense and can provide data at higher rates, which reduces the parts count. Such a configuration is shown in FIG. 4B, for example, in which the 64 or 128 channel ($660_1$–$660_r$) system is configured on one or two printed circuit boards. In this two board system, the T/R circuit and the preamplifier/TGC circuit are fabricated in a single integrated circuit and are placed on one board with a CDP beamformer that is formed as a second integrated circuit. The beamformer control circuits can include the calculation of weighted inputs with processor 670. The memory for this system is either a SDRAM or VRAM located on the second board along with the system controller and the digital communication control circuit.

Returning to FIG. 3A, the standard Fire Wire cable 40 includes a plurality of Fire Wire signal lines 42 and a Fire Wire power line 44. In order to provide the necessary voltages, the Fire Wire power line 44 is fed to an inline DC-DC converter 300. The DC—DC converter 300 generates the necessary voltages and provides them over a plurality of power lines 46. These new power lines 46 are repackaged with the Fire Wire signal lines 42 in a custom cable 40'. In the probe housing 3', the Fire Wire signal lines 42 are connected to the Fire Wire chipset 220 and the custom power lines 46 are connected to a power distributor 48, which filters and distributes the various voltages over respective internal voltage lines 148A, 148B, 248. In addition, the power distributor 48 may perform additional DC-DC conversions, as described in more detail below.

The transmit/receive control chip is needed to interface with the transducer array. In a transmit mode, the chip can provide delays to the high-voltage driving pulses applied to each of the selected transducer elements such that the transmitted pulses will be coherently summed on the image place at the required transmit focus point. In a receive mode, it provides connection of the reflected sound waves received by a selected element to its corresponding amplifier. The functions of a multi-channel transmit/receive chip can be separated into two parts: a core function which provide low-voltage transmit/receive control and a buffer function which level shifts the low-voltage transmit/receive control into high voltage and directly interfaces with the transducer array. The core function of the transmit/receive chip includes a global counter which broadcasts a master clock and bit values to each channel processor; a global memory which controls transmit frequency, pulse number, pulse sequence and transmit/receive select; a local comparator which provides delay selection for each channel. For example, for a 60 MHz clock and a 10 bit global counter, it can provide each channel with up to 17 us delay; a local frequency counter which provides programmable transmit frequency; a local pulse counter which provides different pulse sequences. For example, a 7-bit counter can provide programmable transmitted pulse lengths from one pulse up to 128 pulses; a locally programmable phase selector which provides subclock delay resolution. For example, for a 60 MHz master clock and a two-to-one phase selector provides 8 ns delay resolution.

While typically the period of the transmit-chip clock determines the delay resolution, a technique called programmable subclock delay resolution allows the delay resolution to be more precise than the clock period. With programmable subclock delay resolution, the output of the frequency counter is gated with a phase of the clock that is programmable on a per-channel basis. In the simplest form, a two-phase clock is used and the output of the frequency counter is either gated with the asserted or Deasserted clock. Alternatively, multiple skewed clocks can be used. One per channel can be selected and used to gate the coarse timing signal from the frequency counter.

Figure 3C:
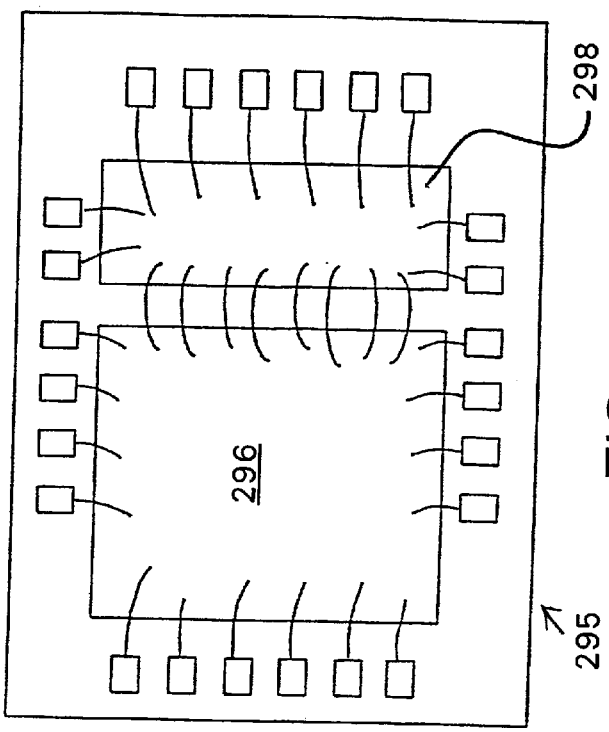
FIGS. 3B and 3C illustrate embodiments of the transmit/receive circuit.
Figure 3B:
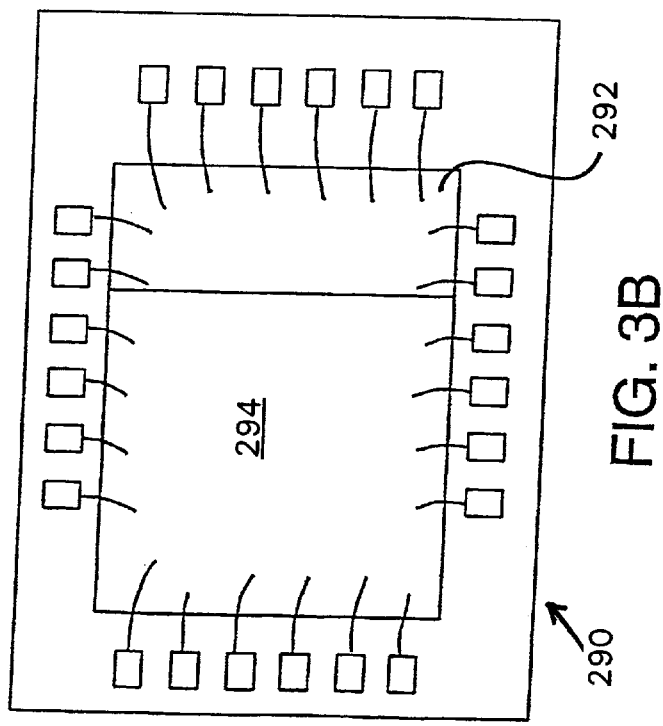

As can be seen in FIG. 3B, a semiconductor process that can support both high-voltage and low-voltage operations is ideally matched for a single-chip solution to the transmit/receive chip described above. The core function of the transmit/receive chip can be implemented on low-voltage transistors to reduce power consumption. The level-shifting function can be implemented on high-voltage transistors to provide the necessary driving pulses to the transducer array. However, only selected semiconductor processes can make the integration of both high-voltage (buffer 292) and low-voltage transistors (294) on one chip 290 possible. As a result, the high/low voltage process has been so far offered only with 0.8-to-1 um-design rules. With these design rules, a 64-channel transmit/receive chip can easily be integrated on a single chip in less than 1 cm² chip area.

In order to save power and silicon area, a multi-chip module 295 can be used to implement a transmit/receive chip. For example, a deep-sub-micron process can be used to implement the core function 296 of the module, and a separate process can be used to implement the buffer 298 function. As shown in FIG. 3C, the multi-chip set can be mounted in a single package to realize the transmit/receive control function. With multi-chip module approach, a 128-channel transmit/receive controller can easily be integrated on one package.

Figure 3D:
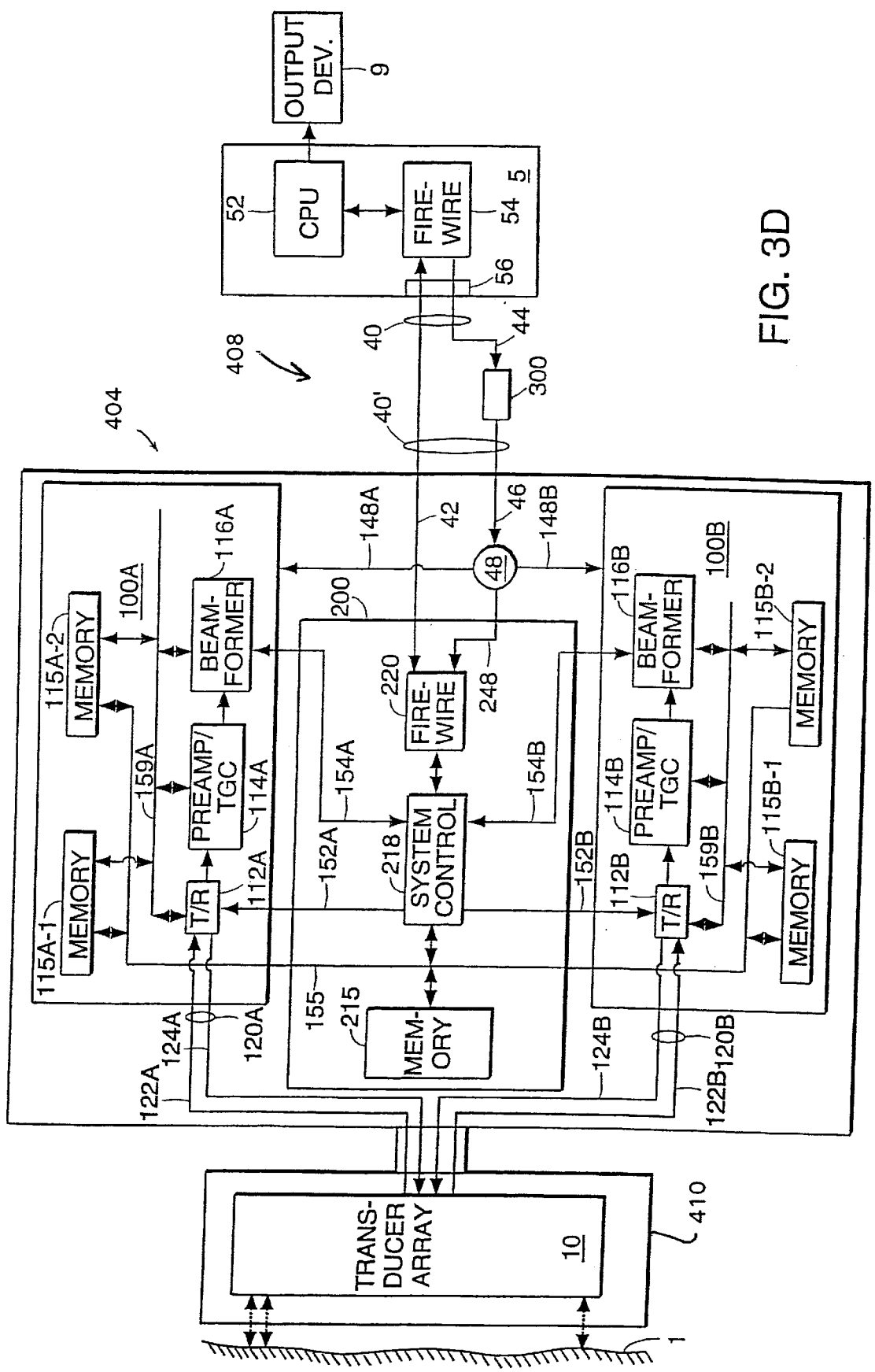
FIG. 3D illustrates an alternate embodiment in which the probe housing is separated from the interface housing by a cable.

FIG. 3D illustrates an alternate embodiment in which the transducer array 10' is located in a separate probe housing 410 connected to the interface housing 404 by a cable 412. Such a system is also illustrated in connection with FIG. 12. Note that another embodiment involves a probe housing in which certain circuit elements such as the transmit/receive circuitry and/or the preamp/TGC circuitry is included with the transducer array while the beamformer, system control and memory circuits remain in the interface. The system in FIG. 3D provides for the use of standard probes and a beamformer interface that weighs less than 10 lbs and which can be connected to a standard personal computer. The interface 404 has a volume of less than 1500 cm³ and a weight that is preferably less than 5 lbs.

Figure 6:
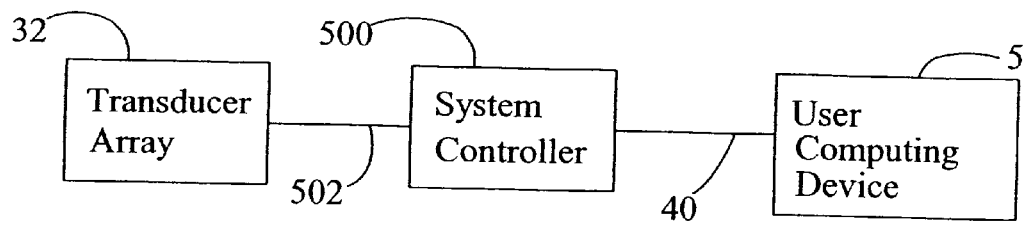
FIG. 6 shows a block diagram of an ultrasonic imaging system adapted for external application integration as defined by the present claims.

FIG. 6 shows a block diagram of another particular embodiment of an ultrasonic imaging system adapted for external application integration. Referring to FIG. 6, the transducer array housing 32 and associated circuitry are connected to a system controller 500 via an ultrasound (US) interface 502. The system controller 500 is connected to a host user computing device 5 such as a PC via a standard interface 40 which is a predetermined communication link, such as an IEEE 1394 interface, also known as Firewire. The US data therefore, is transmitted to a user computing device 5 via the standard interface 40, relieving the need for specialized components to be employed in the user computing device 5. The user computing device 5 therefore provides an ultrasonic application server which may be integrated with an external application, as will be described further below.

The ultrasonic application server running on the user computer device 5, therefore, receives the US data, and makes it available to be invoked by an external application for further processing. The external application may be either local, and therefore running on the user computer device 5, or remote, and accessing the ultrasonic application server remotely.

Figure 7A:
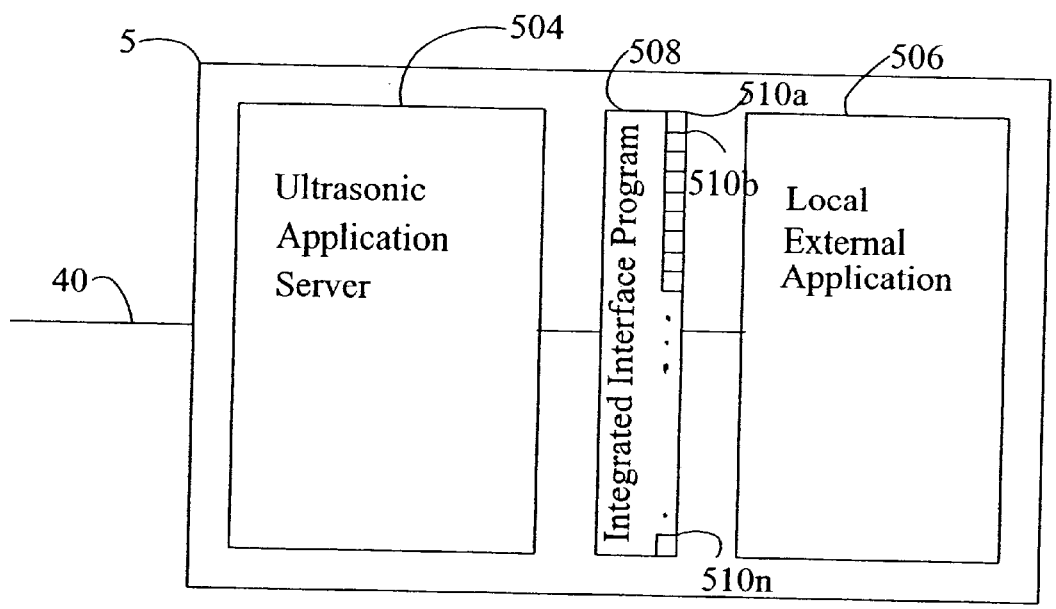
FIG. 7A shows an integrated interface program operable for use with a local external application.

FIG. 7A shows an integrated interface program operable for use with a local external application. Referring to FIG. 7A, the ultrasonic application server 504 is running on the user computing device 5. A local external application 506 is also running on the user computing device 5, and transmits to and from the ultrasonic application server 504 via an integrated interface program 508. The integrated interface program 508 contains a series of predetermined entry points 510a . . . 510n corresponding to operations which the ultrasonic application server 504 may perform on behalf of the local external application 506. The local external application 506 sends a command, which includes an instruction and optional parameters as defined by the predetermined entry points 510. The local external application 506 transmits the command to the ultrasonic application server 504 by invoking the entry point 510n in the integrated interface program which corresponds to intended operation. The entry point may be invoked by procedure or function call via a stack call, message transmission, object passing, or other suitable interprocess communication mechanism. In a particular embodiment, Windows® messages may be used.

The command is received by the ultrasonic application server 504 via the desired entry point 510n from the integrated interface program 508, and is processed. The ultrasonic application server 504 executes a result corresponding to the desired function, and transmits the result back to the external application 506 via the integrated interface program 508, typically by similar interprocess communication mechanisms employed in transmitting the corresponding command. The operations performed by the ultrasonic application server may include the following:

| OPERATION | DESCRIPTION |
|---|---|
| Freeze Image | Freeze active ultrasound data image; used to capture still frames |
| Resume Live | Obtain realtime ultrasound image |
| Export Frame | Export a frame of ultrasound image data in a format as determined by the parameters |
| Application Status | Return a status code of a previous operation |
| Initialize | Initialize Ultrasonic Application Server to begin receiving commands from an external application |
| Exit Application | Disconnect external application from the Ultrasonic Application Server | and may also include others by defining an entry point in the integrated interface program 508 and a corresponding operation in the ultrasonic application server 504.

The result received by the local external application 506, therefore, may be employed and analyzed by any functions provided by the local external application 506. The local external application 506 may be extended and modified to provide desired functions without modifying the ultrasonic application server 504 or the integrated interface program 508. Further, additional entry points 510n to other operations provided by the ultrasonic application server 504 may require only modification of the integrated interface program 508. Further, multiple external applications may access the integrated interface program 508 by computing the proper instructions and parameters of the commands as defined by the integrated interface program 508.

In particular embodiments, the external application is operable to process 2 dimensional and 3 dimensional radiation therapy data, fetal image data, cardiac image data, and image guided surgery data. Such applications are employed in the medical field by operators such as surgeons to provide visual feedback about medical information. For example, fetal image data is used to view a fetus in utero. By employing multidimensional data to provide a visual image, conditions such as birth defects, treatable ailments, gender, size, and others can be determined. Similarly, radiation therapy data may be employed to simultaneously display information about the direction and intensity of radiation treatment, and a visual image of the treatment area. Such visual image data may also be employed in image guided surgery, to indicate the location of a surgical instrument. Such information is particularly useful in contexts such as brain surgery, where it may not be possible to expose the afflicted area.

Figure 7B:
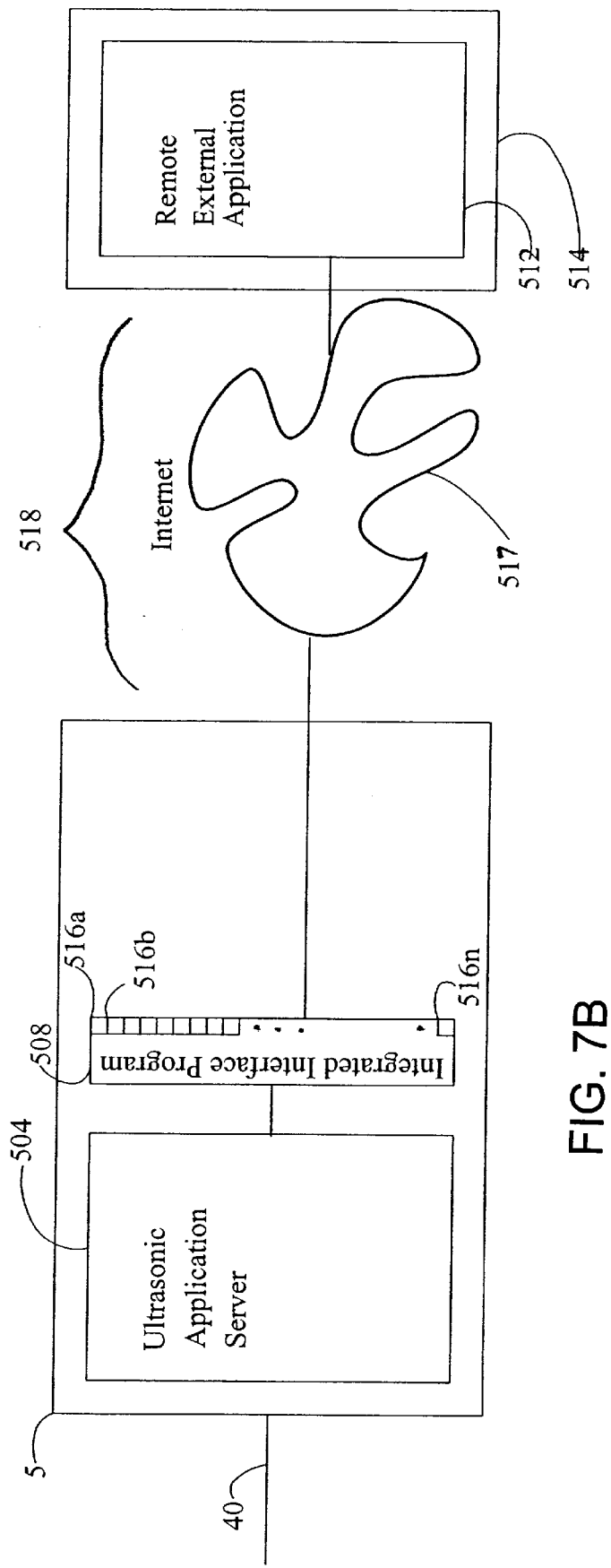
FIG. 7B shows an integrated interface program operable for use with a remote external application.

FIG. 7B shows an integrated interface program 508 operable for use with a remote external application. In such an embodiment, a remote external application 512 is running on a remote computing device 514 such as a PC, and is connected to the user computing device 5 via a public access network 517 such as the Internet via a communication link 518. The integrated interface program 508 includes connection points 516a . . . 516n such as remote procedure call (RPC) points or other inter-node communication mechanism. In a particular embodiment the connection points are sockets in accordance with the TCP/IP protocol.

Similar to the local external application 506, the remote external application 512 is operable to compute a command corresponding to an intended operation in the ultrasonic application server 504. The connection points 516n are generally operable to receive a command transmitted from the remote external application 512. The ultrasonic application server 504 sends a result corresponding to the command, and transmits the result back to the remote external application 512 via the integrated interface program 508 by an inter-node communication mechanism such as that used to transmit the command. Further, the same integrated interface program could have both entry points 510n, generally to be accessed by the local external application 506, and connection points 516n, generally accessible by the remote external application 512.

Figure 8:
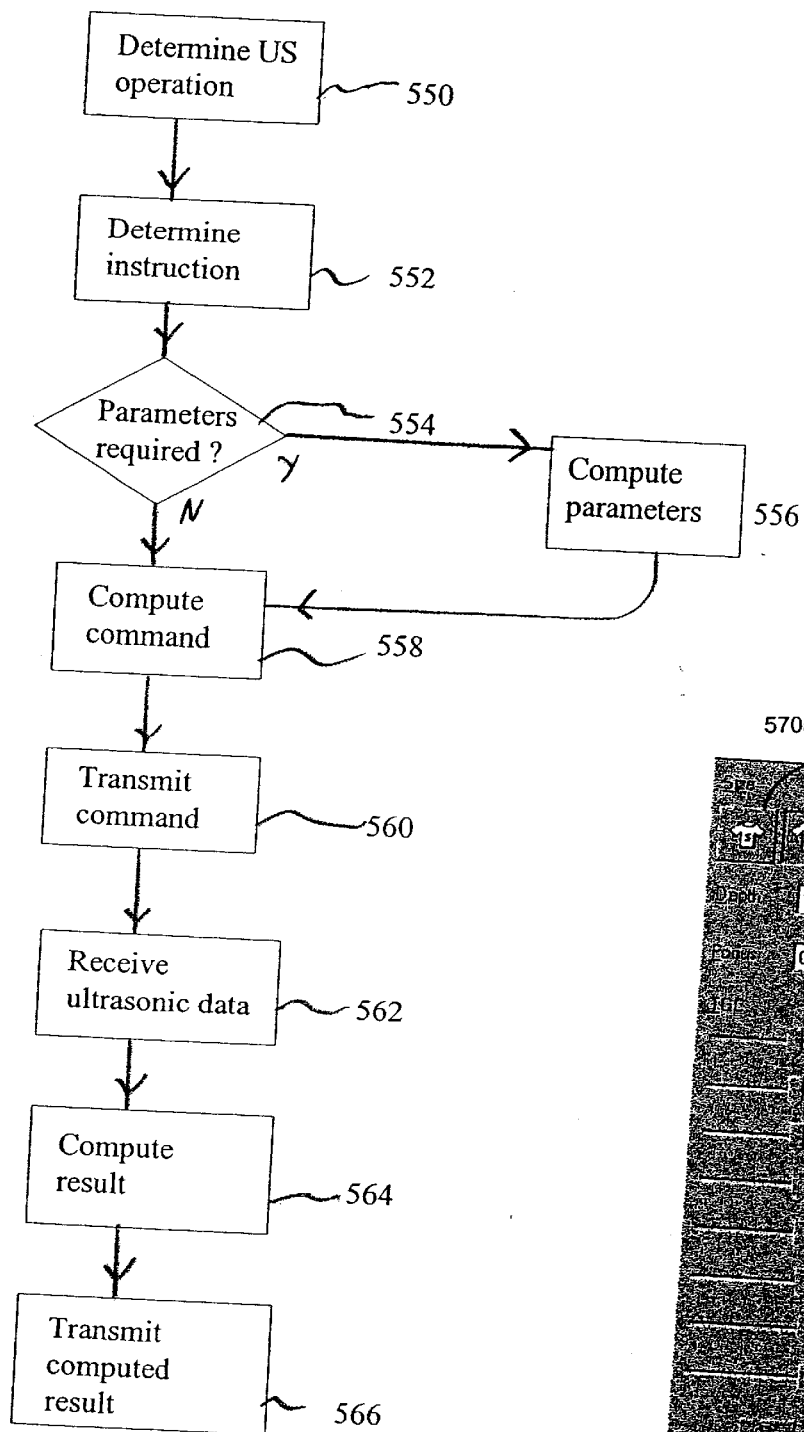
FIG. 8 shows a flowchart of external application integration as defined herein.

FIG. 8 shows a flowchart of external application integration. Referring to FIGS. 6, 7A, 7B and 8, an external application determines a desired US operation to be employed in processing and/or analysis, as depicted at step 550. The operation may provide data, and may cause a certain result or state change, or a combination. The external application determines the instruction corresponding to this operation, as shown at step 552, as defined by the integrated interface program. The external application then determines if any parameters are required for the operation, as disclosed at step 554. If parameters are required, the external application determines the parameters, as depicted at step 556. If no parameters are required, execution continues. The external application determines a command including the instruction and any required parameters, corresponding to the desired US operation, as shown at step 558. The command is transmitted to the ultrasonic application server via the integrated interface program, as disclosed at step 560. The transmission may be by any suitable method, such as those described above and others, depending on whether the external application is local or remote.

Ultrasonic data is received by the ultrasonic application server 504 via the standard communication interface 40 indicative of ultrasonic image information, as depicted at step 562. As described above, the ultrasonic data is received via a test probe disposed in contact with the subject, or patient, for viewing such visual information as radiation therapy data, fetal image data, cardiac image data, and image guided surgery data. Information such as the ultrasonic application server 504 executes a result corresponding to the command from the ultrasonic data, as disclosed at step 564. Thus step 564 may involve control signals being generated to define or re-define a region of interest in which radiation is to be directed for treatment. The ultrasonic application server 504 then transmits the computed result to the external application via the integrated interface program 508, as shown at step 566. Note that it is expected that many successive command and results are computed, and the ultrasonic data is concurrently sent in an iterative manner over the standard communication interface 40.

In another particular embodiment, the integrated application program includes both entry points for local external applications, and connection points for remote external applications. The instructions and parameters corresponding to the entry points are known to the local external application, and the instruction and parameters corresponding to the connection points are known to the remote external application. Further, there may be both an entry point and a connection point operable to invoke the same operation in the integrated application server. In such an embodiment, a semaphore or reentrancy mechanism is employed in the ultrasonic application server to avoid deadlock or simultaneous attempts to invoke the same operation. Both the local and remote external applications invoke the ultrasound application server via the integrated interface program 508 (FIGS. 7A and 7B).

Figure 9:
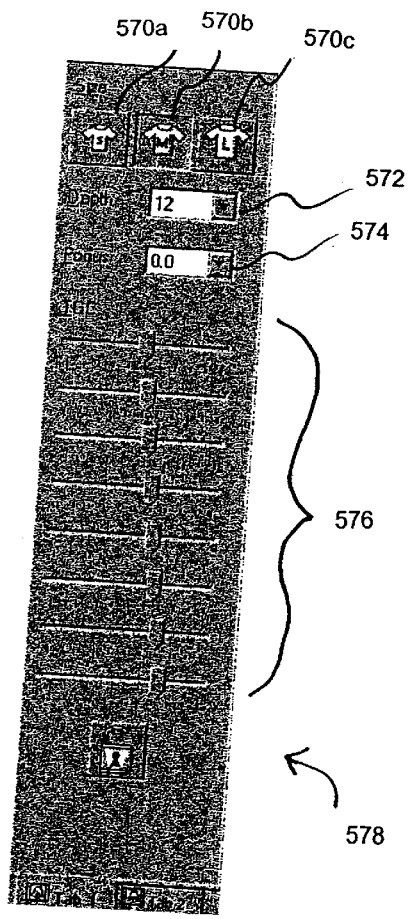
FIG. 9 shows a graphical user interface (GUI) for use with the ultrasonic imaging system as defined herein.

The ultrasonic application server also includes a graphical user interface for manipulating operations without accessing the external application. Referring to FIG. 9, a control bar 578 of a top level GUI screen is shown. The control bar allows manipulation of tools affecting image settings of the display via image control presets. The image settings are controlled for each of three sizes small 570a, medium 570b, and large 570c. For each size, the image settings within that size may be controlled, including depth 572, focus 574, and time gain compensation 576. Each of these settings may be saved under a user defined name for later recall. The user clicks on a save button and is prompted to enter a file name. Each of the three sets of image settings corresponding to the size settings 570a, 570b, and 570c is then stored corresponding to the file name, and may be recalled by the user at a later time.

Those skilled in the art should readily appreciate that the programs defining the operations and methods defined herein are deliverable to a user computing device and a remote computing device in many forms, including but not limited to a) information permanently stored on non-writeable storage media such as ROM devices, b) information alterably stored on writeable storage media such as floppy disks, magnetic tapes, CDs, RAM devices, and other magnetic and optical media, or c) information conveyed to a computer through communication media, for example using baseband signaling or broadband signaling techniques, as in an electronic network such as the Internet or telephone modem lines. The operations and methods may be implemented in a software executable by a processor or as a set of instructions embedded in a carrier wave. Alternatively, the operations and methods may be embodied in whole or in part using hardware components, such as Application Specific Integrated Circuits (ASICs), state machines, controllers or other hardware components or devices, or a combination of hardware, software, and firmware components.

Figure 10:
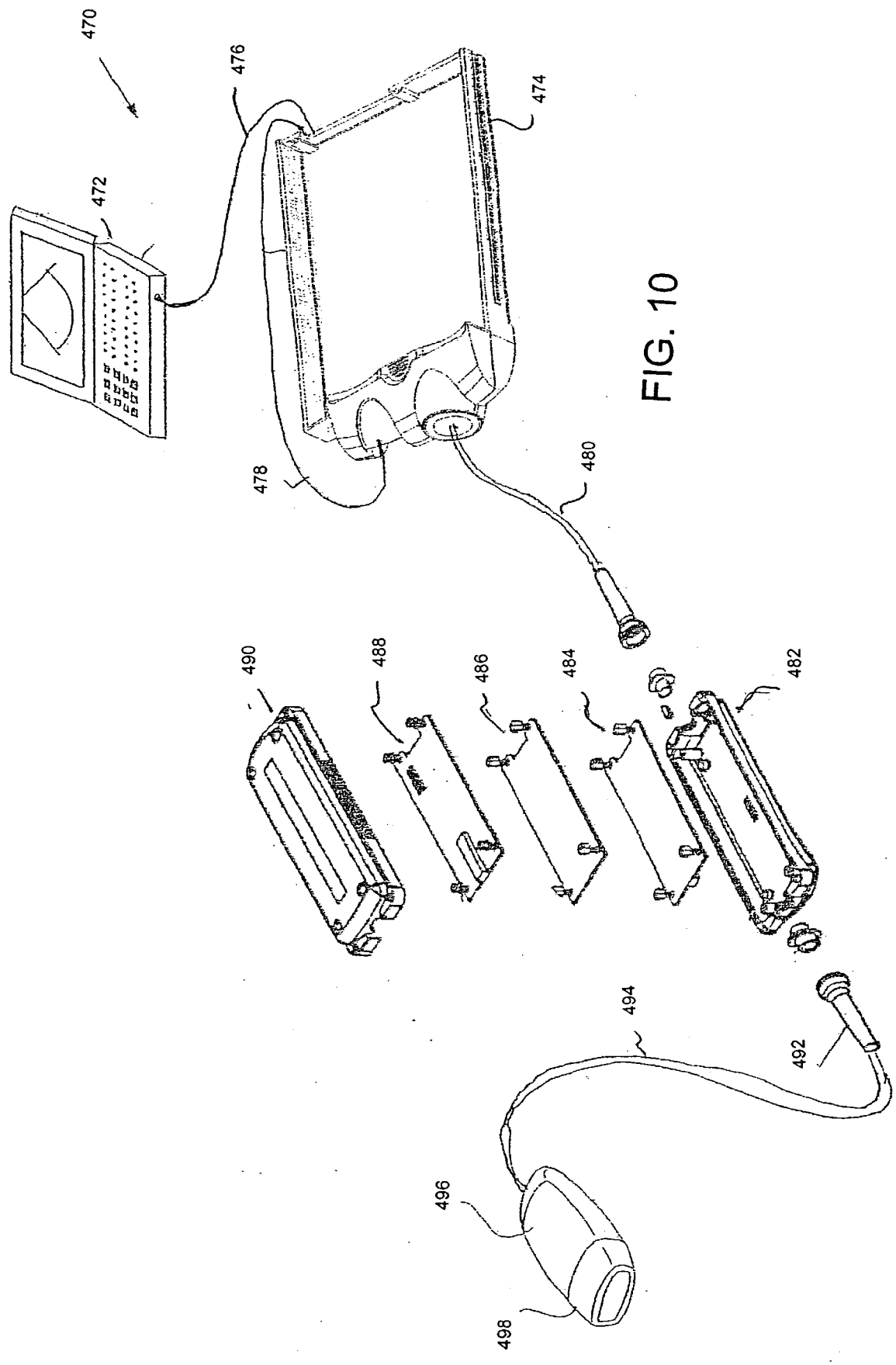
FIG. 10 is a preferred embodiment of a portable ultrasound system in accordance with the invention.

FIG. 10 illustrates a preferred embodiment of a portable ultrasound system 470 in accordance with the invention. A personal computer 472 such as a laptop, a hand held computer or a desktop workstation can provide power and a standard interface (e.g. IEEE 1394 or USB) to a housing 474 along cable 476. Housing 474 includes a DC-DC converter to deliver power along cable 480 to interface housing (482,490). This interface housing has two or three circuit boards 484, 486, 488 as described previously. A standard transducer housing 496 with transducer array 498 is connected to the interface housing along cable 494 and connector 492. The beamformer integrated circuit mounted on circuit board 486 requires steering data, the transmit circuitry requires data to provide proper transmit focus and the TGC must have gain level information for a given depth.

Figure 11:
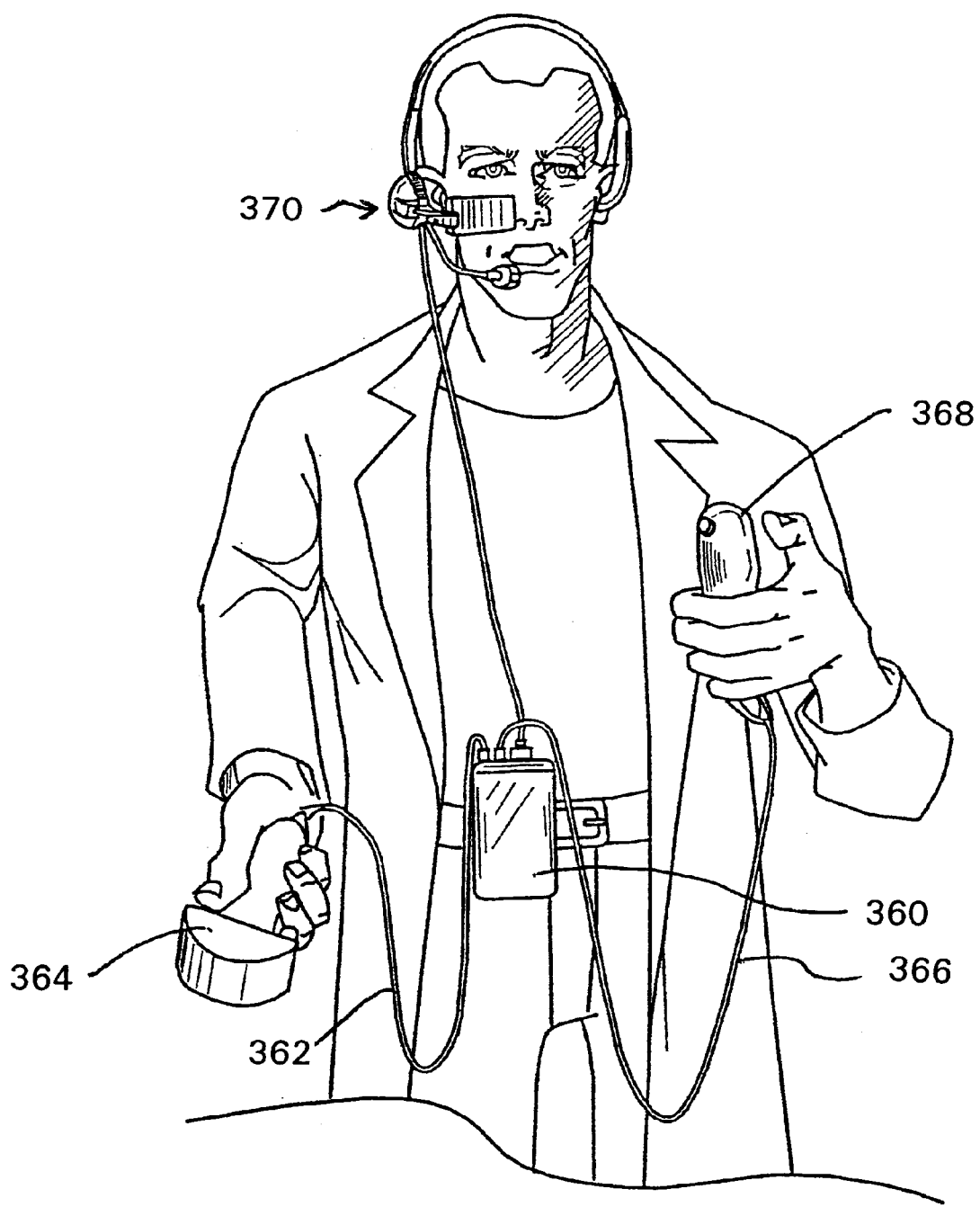
FIG. 11 illustrates a wearable or body mounted ultrasound system in accordance with the invention.

FIG. 11 illustrates a wearable ultrasound imaging system that can include a belt mounted computer 360 or interface connected big cable 362 to handheld probe 364, a second handheld unit 366 that can include various controls including a mouse control and buttons to freeze the image displayed or to store a particular image in electronic memory. The unit 366 can be connected by wireless (RF or infrared) connection or by cable 366 to housing 360. The computer 360 can be connected to a desktop, laptop or handheld display or can be connected by cable to a headmounted display system 370 that includes a microphone, a pair of speakers for audio and a high resolution display positioned adjacent the user's eye.

Figure 12:
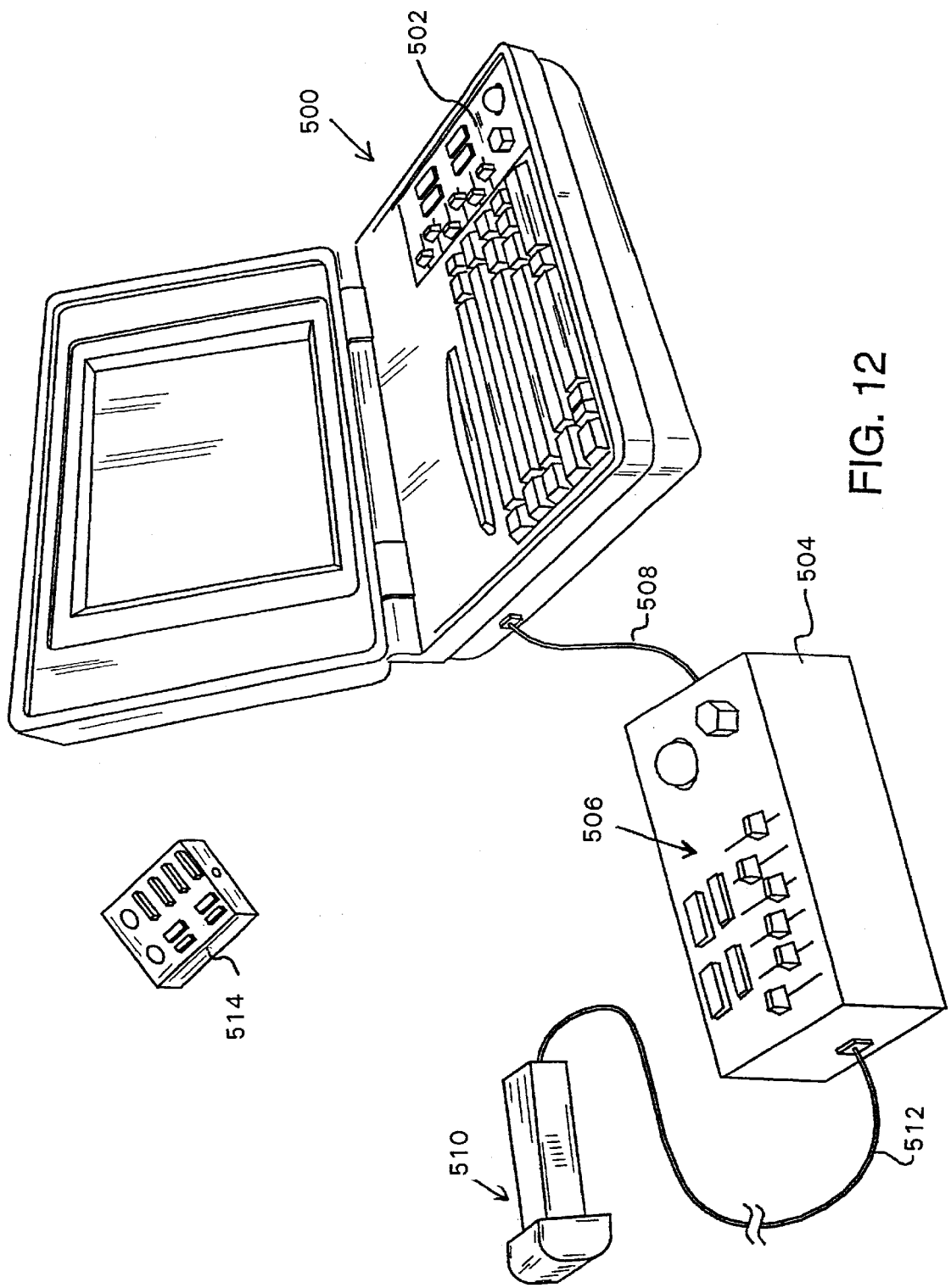
FIG. 12 illustrates an interface system using a standard communication link to a personal computer.

Another preferred embodiment is illustrated in FIG. 12 in which a laptop computer 500, having a flat panel display and a standard keyboard, has been programmed to perform scan conversion, doppler processing etc. on a beamformed representation of the region of interest that has been transmitted from interface housing 504 along a standard communications link such as cable 508 that conforms to the IEEE 1394 Firewire standard or the USB 2.0 standard, for example. The computer 500 and/or the interface can optionally include a control panel 502,506, that can be used to control the study being conducted. A preferred embodiment of the interface housing 504 is controlled solely by the personal computer 500 and provides for the use of standard transducer array probes that can be interchangeably attached to the interface housing 504 with a cable. Alternately, an additional remote controller 514 can be used to control system operation. The interface 504 can house the circuit boards on which the beamformer, memory, system controller and digital communication circuits are mounted. The interface 504 is connected to the handheld probe 510 with a cable that is preferably between two feet and six feet in length, however longer lengths can be used. The transmit/receive and/or the preamplifier/TGC circuits can be in the probe housing 510 or in the interface housing 504. The computer can also be configured for gigabit ethernet operation and for transmitting video and image data over networks to remote systems at clinics or hospitals. The video data can also be sent to a VCR or standard video recorder or video camera with an IEEE 1394 part for recording on videotape. The VCR or video camera can be controlled using the computer.

Returning to FIG. 1, the host 5 can be a desktop, laptop palmtop or other portable computer executing software instructions to display ultrasound images. In addition to real-time B-mode ultrasound images for displaying soft-tissue structures in the human body, Doppler ultrasound data can be used to display an estimate of blood velocity in the body in real time. Three different velocity estimation systems exist: color-flow imaging (CFI), power-Doppler and spectral sonogram.

The color-flow imaging modality interrogates a specific region of the body, and displays a real-time image of mean velocity distribution. The CFI's are usually shown on top of the dynamic B-mode image. To determine the direction of blood flow, different colors indicate velocity toward and away from the transducer.

While color flow images display the mean or standard deviation of the velocity of reflectors (i.e., blood cells) in a given region, power Doppler (PD) displays a measurement of the amount of moving reflectors in the area, similar to a B-mode image's display of the total amount of reflectivity. A PD image is an energy image in which the energy of the flow signal is displayed. These images give no velocity information but only show the location of flow.

The spectral Doppler or spectral sonogram modality utilizes a pulsed-wave system to interrogate a single range gate and displays the velocity distribution as a function of time. This sonogram can be combined with a B-mode image to yield a duplex image. Typically, the top side of the display shows a B-mode image of the region under investigation, and the bottom shows the sonogram. Similarly, the sonogram can also be combined with the CFI image to yield a triplex image. Thus, the time for data acquisition is divided between acquiring all three sets of data. Consequently, the frame rate of the complex image is generally decreased, compared to either CFI or duplex imaging.

A pulsed-Doppler processor for color-flow map applications is now described. Color Doppler (CD) or color-flow imaging combines, in a single modality, the capabilities of ultrasound to image tissue and to investigate blood flow. CD images consist of Doppler information that can be color-encoded and superimposed on a B-mode gray-scale image.

Color-flow imaging is a mean velocity estimator. There are two different techniques in computing the mean velocity. First, in a pulsed Doppler system fast fourier transformer (FFTs) can be used to yield the velocity distribution of the region of interest, and both the mean and variance of the velocity profile can be calculated and displayed as a color flow image. The other approach uses a one-dimensional auto correlation.

An estimate of the mean velocity in the range gate gives an indication of the volume flow rate. Given that the frequency of the reflected, range-gated signal is proportional to the flow velocity, the spatial mean velocity is determined by the mean angular frequency.

$$\bar{\omega} = \frac{\int_{-\infty}^{+\infty} \omega P(\omega) d\omega}{\int_{-\infty}^{+\infty} P(\omega) d\omega} \quad (1)$$

Here, $P(\omega)$ is the power-spectral density of the received, demodulated signal. The inverse Fourier transform of the power-spectral density is the autocorrelation:

$$R(\tau) = \int_{-\infty}^{+\infty} P(\omega) \exp(j\omega\tau) d\omega. \quad (2)$$

The derivative of the autocorrelation with respect to $\tau$ is:

$$R(\tau) = \int_{-\infty}^{+\infty} P(\omega) \exp(j\omega\tau) d\omega \quad (3)$$

Substituting Eqs. (2) and (3) into Eq. (1) yields:

$$\bar{\omega} = \frac{R(0)}{jR(0)}. \quad (4)$$

Therefore, the mean velocity estimator can be reduced to an estimation of the autocorrelation and the derivative of the autocorrelation. The estimator given by the proceeding expression can be calculated when data from two returned lines are used, i.e., $$\bar{\omega} = -f_{prf} arc\tan(\Phi) \quad (5)$$

where $$\Phi = \frac{\frac{1}{N_c - 1} \sum_{i=0}^{N_c - 2} y(i+1)x(i) - x(i+1)y(i)}{\frac{1}{N_c - 1} \sum_{i=0}^{N_c - 2} x(i+1)x(i) + y(i+1)y(i)} \quad (6)$$

$f_{prf}$ is the pulse repetition frequency, and $N_C$ are the number of lines used in autocorrelation estimator. In practice, more then 2 lines are used to improve the signal-to-noise ratio. Data from several RF lines are needed in order to get useful velocity estimates by the auto-correlation technique. Typically, between 8 and 16 lines are acquired for the same image direction. The lines are divided into range gates throughout the image depths and the velocity is estimated along the lines.

For duplex imaging, the CFI pulses are interspersed between the B-mode image pulses. For CFI pulses, it is known that a longer duration pulse train gives an estimator with a lower variance, however, good spatial resolution necessitates a short pulse train. Consequently, a separate pulse train must be used for the B-mode image, because the CFI pulse train is too long for high-resolution, gray-scale images.

For color-flow imaging, CFI, the velocity estimator is given by Eq. (5). This can be computed by serial processing, since the arrival of samples for a new line results in the addition of the new data to an already calculated sum. Four multiplications, three additions, and a subtraction are performed for each range gate and each new line. Stationary echo cancellation is also performed for each new sample. A filter with $N_e$ coefficients necessitates $2N_e$ multiplications and additions per gate and line.

Assuming that all data samples are used for CFI imaging, the total number of multiplications and additions per second is $$N_{ops} = (2N_e + 2)Mf_0 \quad (7)$$

where $Mf_0$ is the number of data samples per second. This is a conservative value since B-mode lines are interspersed with CF imaging lines causing time to be lost switching between modes. It follows that $$N_{ops} = \eta(nN_e + 2)Mf_0 N_c - \frac{N_b}{N_c}, \quad (8)$$

where $N_c$ is the number of CFI lines per estimate, $N_B$ is the number of B-mode image lines interspersed between CFI lines, and $\eta$ denotes the effective time spent on acquiring useful data.

For a CFI system using 8 lines per estimate, an echo cancellation filter with 4 coefficients and an 8 timesoversampled 4 MHZ pulse, one B-mode line is interspersed between CFI lines and 80% of the time is consumed acquiring data. Using Eq. (7), the number of calculations per second is $N_{ops}=172\times10^6$. This is within the capability of a current Pentium-class laptop computer. Thus, all of the CFI signal processing can be performed in software using a state-of-the-art microprocessor.

While Color Flow Imaging (CFI) has been an effective diagnostic tool in clinical cardiovascular applications, Power Doppler (PD) imaging provides an alternative method of displaying the blood stream in the insonified regions of interest. While CF imaging displays the mean or standard deviation of the velocity of reflectors (e.g., blood cells) in a given region, PD displays a measurement of the density of moving reflectors in the area, similar to the B-mode image's display of reflectivity. Thus, Power Doppler is akin to a B-mode image with stationary reflectivity suppressed. This is particularly useful for viewing moving particles with small cross-sectional scattering, such as red blood cells.

Power Doppler displays the integrated Doppler power instead of the mean frequency shift as used for color Doppler imaging. As discussed in the previous section, the color-flow mapping is a mean-frequency estimator that is expressed as $$\bar{\omega} = \frac{\int_{-\infty}^{+\infty} \omega P(\omega)\,d\omega}{\int_{-\infty}^{+\infty} P(\omega)\,d\omega} \qquad (9)$$

where $\bar{\omega}$ represents mean-frequency shift and $P(\omega)$ is the power-spectral density of the received signal. The inverse Fourier transform of the power-spectral density is the auto-correlation:

$$R(\tau) = \int_{-\infty}^{+\infty} P(\omega)\exp(j\omega\tau)\,d\omega. \qquad (10)$$

The total Doppler power can be expressed as the integral of the power-spectral density over all angular frequencies, $$pw = \int_{-\infty}^{+\infty} P(\omega)\,d\omega. \qquad (11)$$

By observing the similarities between Eq. (2) into (10), it follows that the 0th lag of the auto-correlation function can be used to compute the integrated total Doppler power.

$$R(0) = \int P(\omega)\exp(j\omega 0)\,d\omega = \int P(\bar{\omega})\,d\omega = pw \qquad (12)$$

In other words, the integrated power in the frequency domain is the same as the integrated power in the time domain and hence the power Doppler can be computed from either the time-domain or the frequency-domain data. In either case, the undesired signals from the surrounding tissue, such as the vessel walls, should be removed via filtering. This calculation is also referred to as a Wall filter.

In a preferred embodiment, the PD can be computed in software running on a microprocessor; similar to the computation of the CFI processing described above. Parallel computation units, such as those in the Intel Pentium TM and Pentium II's MMX coprocessors, allow rapid computation of the required functions. A Digital Signal Processor (DSP) can also be used to perform this task. For either case, a software implementation permits the flexibility to change and investigate digital signal processing algorithms and transmitting signals that achieve the best performance as region of interest changes.

The above showed that the frequency content of the Doppler signal is related to the velocity distribution of the blood. It is common to devise a system for estimating blood movement at a fixed depth in tissue. A transmitter emits an ultrasound pulse that propagates into and interacts with tissue and blood. The backscattered signal is received by the same transducer and amplified. For a multiple-pulse system, one sample is acquired for each line or pulse emitted. A display of the distribution of velocities can be made by Fourier transforming the received signal and showing the result. This display is also called a sonogram. Often a B-mode image is presented along with the sonogram in a duplex system, and the area of investigation, or range gate, is shown as an overlay on the B-mode image. The placement and size of the range gate is determined by the user. In turn, this selects the epoch for data processing. The range gate length determines the area of investigation and sets the length of the emitted pulse.

The calculates spectral density is displayed on a screen with frequency on the y-axis and time on the x-axis. The intensity of a pixel on the screen indicates the magnitude of the spectrum; thus, it is proportional to the number of blood scatterers moving at a particular velocity.

The range gate length and position are selected by the user. Through this selection, both emitted pulse and pulse repetition frequency are determined. The size of the range gate is determined by the length of the pulse. The pulse duration is $$T_p = \frac{2l_g}{c} = \frac{M}{f} \qquad (13)$$

where the gate length is $l_g$ and M is the number of periods. The gate duration determines how rapidly pulse echo lines can be acquired. This is referred to as the pulse-repetition frequency or $$f_{prf} \le \frac{c}{2d_0}, \qquad (14)$$

where $d_0$ is the distance to the gate. For example, a 4 period, 7 MHz pulse is used for probing a blood vessel lying at a depth of 3 cm with a 10 ms observation time. The gate length is computed as $$l_g = 0.44 \text{ mm} \qquad (15)$$

The pulse-repetition frequency is $$f_{prf} \le \frac{c}{2d_0} \approx 25 \text{ KHz.} \qquad (16)$$

The total number of independent spectral lines is $N = T_{obs} f_{prf} = 250$. It follows that the maximum detectable velocity is $$v_{max} = \frac{f_{prf}}{2} \frac{c}{2f_0} = 1.4 \text{ m/s.} \qquad (17)$$

Using a 256-point FFT to compute the Fourier transform, the total number of multiplications/additions per second required for the preceding example is less than 10 MOPs/s. In a preferred embodiment, the sonograph computation can be carried out in software running on a microprocessor (similar to the computation of the CFI processing described above). Parallel computation units, such as those inside the Intel Pentium TM and Pentium II's MMX coprocessors, allow rapid computation of the required FFT functions. All three velocity estimation systems can be implemented in software on current microprocessors, such as the Intel Pentium, or digital signal processors (DSP).

Methods employing contrast agents have been developed to enhance certain imaging methods. Stabilized microbubbles are used for ultrasound contrast imaging because of their unique acoustic properties compared to biological tissues. They present superior backscattering and nonlinear behavior, and fragility upon exposure to ultrasound. A number of ultrasound imaging modalities have been created to exploit these features.

In fundamental B-Mode imaging, the transmitting and receiving frequencies are the same. The echogenicity of blood is significantly increased with the administration of a contrast material. Gas microbubbles scatter sound much more intensely than an equivalent size liquid or solid particle owing to the acoustic impedance mismatch (particularly the difference in compressibility) between the gas and the surrounding tissue or blood. This effect will be observed in Doppler and M-Mode imaging techniques as well. One disadvantage of using fundamental B-Mode for contrast imaging is that the level of the echoes created by the bubbles is similar to the level of the echoes resulting from the biological tissues.

A technique using the second harmonic relies on the fact that bubbles generate harmonics of the transmitted frequency at a level much higher than the harmonics generated by the tissues. By creating images from the signal received at twice the transmitted frequency, high image contrast is achieved between regions with and without bubbles. A problem with this imaging modality is that a short pulse (typically used in B-mode imaging) has a broad bandwidth and the transmitting and receiving frequencies overlap, contaminating the harmonic image with the fundamental frequency. To alleviate this problem, the pulse length is increased to achieve a narrow bandwidth, however, at the expense of decreasing the axial resolution of the image.

The pulse inversion method (also called wideband harmonic imaging or dual pulse imaging), solves the problem of overlapping frequencies observed with the second harmonic technique. Each scan line is formed by summing the signals received from two ultrasound pulses, where the second pulse is inverted and slightly delayed relative to the first. This procedure cancels the response of all linear scatters (if there is no tissue movement between the two pulses) while enhancing the effects of nonlinear scatterers. Because there is delay between the two pulses, any bubble displacement adds an additional signal, resulting in velocity-dependent enhancement.

Because most ultrasound contrast agents are destroyed by ultrasound irradiation, intermittent or gated imaging techniques have been used. By acquiring an image frame at each cardiac cycle (or after several cardiac cycles), ultrasound exposure is reduced, increasing the longevity of the contrast agents in the region of interest on the image. Another benefit of intermittent imaging is the filling of vascular space during the off-cycle. The degree of filling produces enhancement that is directly related to blood volume of blood flow, since the higher flow rate, the greater the number of bubbles that enters the region of interest, and thus the greater the fractional blood volume.

The stimulated acoustic emission method (also known as transient response imaging) typically involves color Doppler with the transmitting power set high to ensure bubble disruption with the first pulse. When the bubbles collapse, a broadband acoustic signal is generated. Since ultrasound Doppler systems compare the backscattered signal with respect to a "clean" reference signal, this loss of frequency correlation caused by the bubble collapse is interpreted by the machine as a random Doppler shift, resulting in a mosaic of colors at the location of the microbubbles.

A preferred embodiment of the invention employs a spatial filter in providing a power doppler image, for example. This spatial or high pass filter can also be used effectively with a contrast agent to further differentiate between blood flow and the surrounding vessel or artery. First the power is computed and a two pulse canceller is employed. The ratio of the power of the signal before and after the filter provides a data set yielding clear images of moving fluid within the body.

Figure 13:
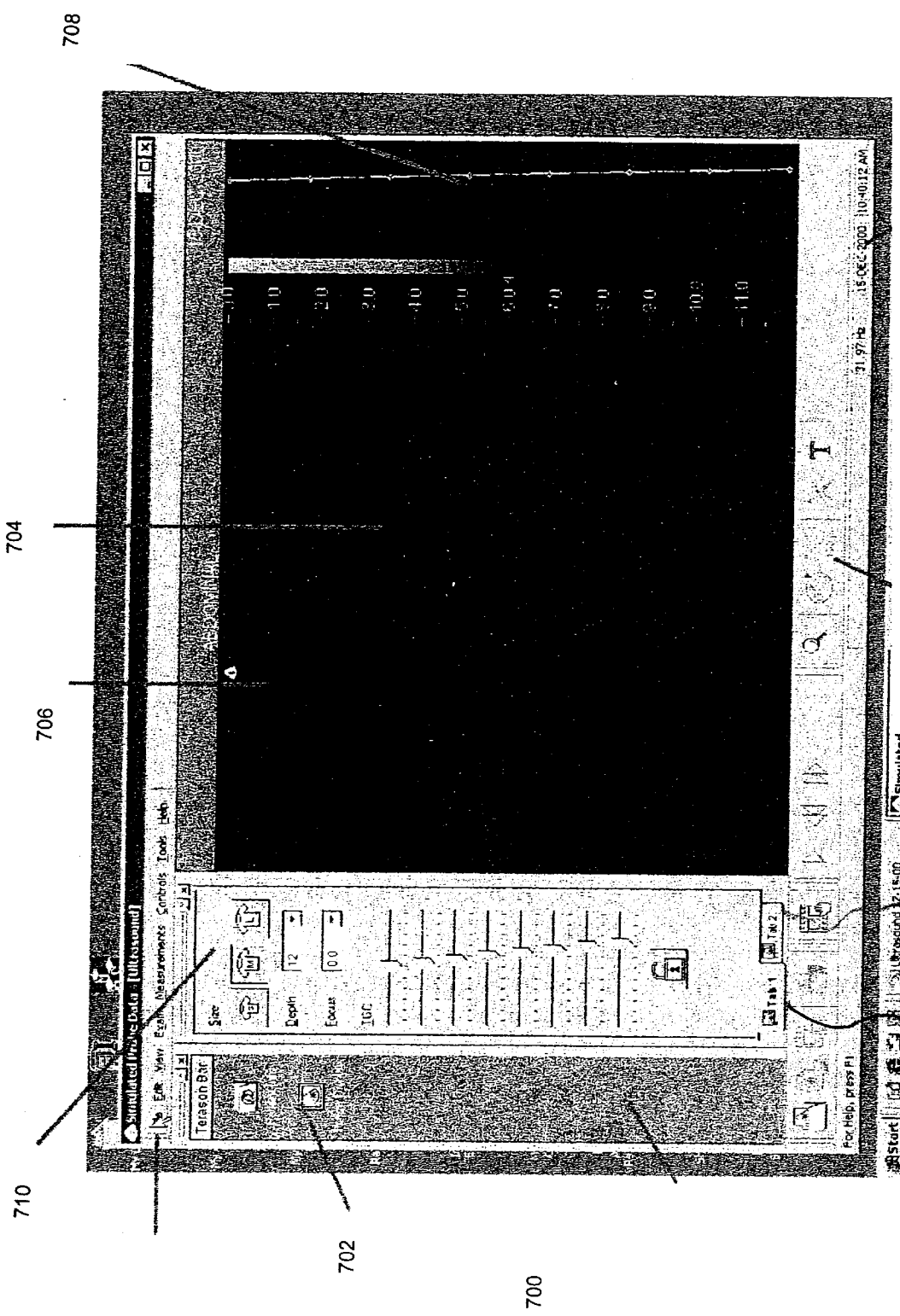
FIG. 13 shows the top-level screen of a graphical user interface (GUI) for controlling the ultrasonic imaging system.

FIG. 13 shows the top-level screen of a graphical user interface (GUI) for controlling the ultrasonic imaging system. Referring to FIG. 13, ultrasonic image data gathered by the hand held probe is displayed and manipulated by the ultrasonic imaging system using this screen. A selection bar 702 allows the operator to select the active focus areas of the screen. An image area 704 displays the ultrasonic image of the subject area. A patient information area 706 displays information about the subject from whom ultrasonic data is being gathered. A Time Gain Compensation area 708 provides feedback about time gain compensation, described further below. A control bar 710 allows qualitative and quantitative selection of ultrasonic imaging operations, as will be described further below with respect to FIGS. 15a and 15b.

Figure 14:
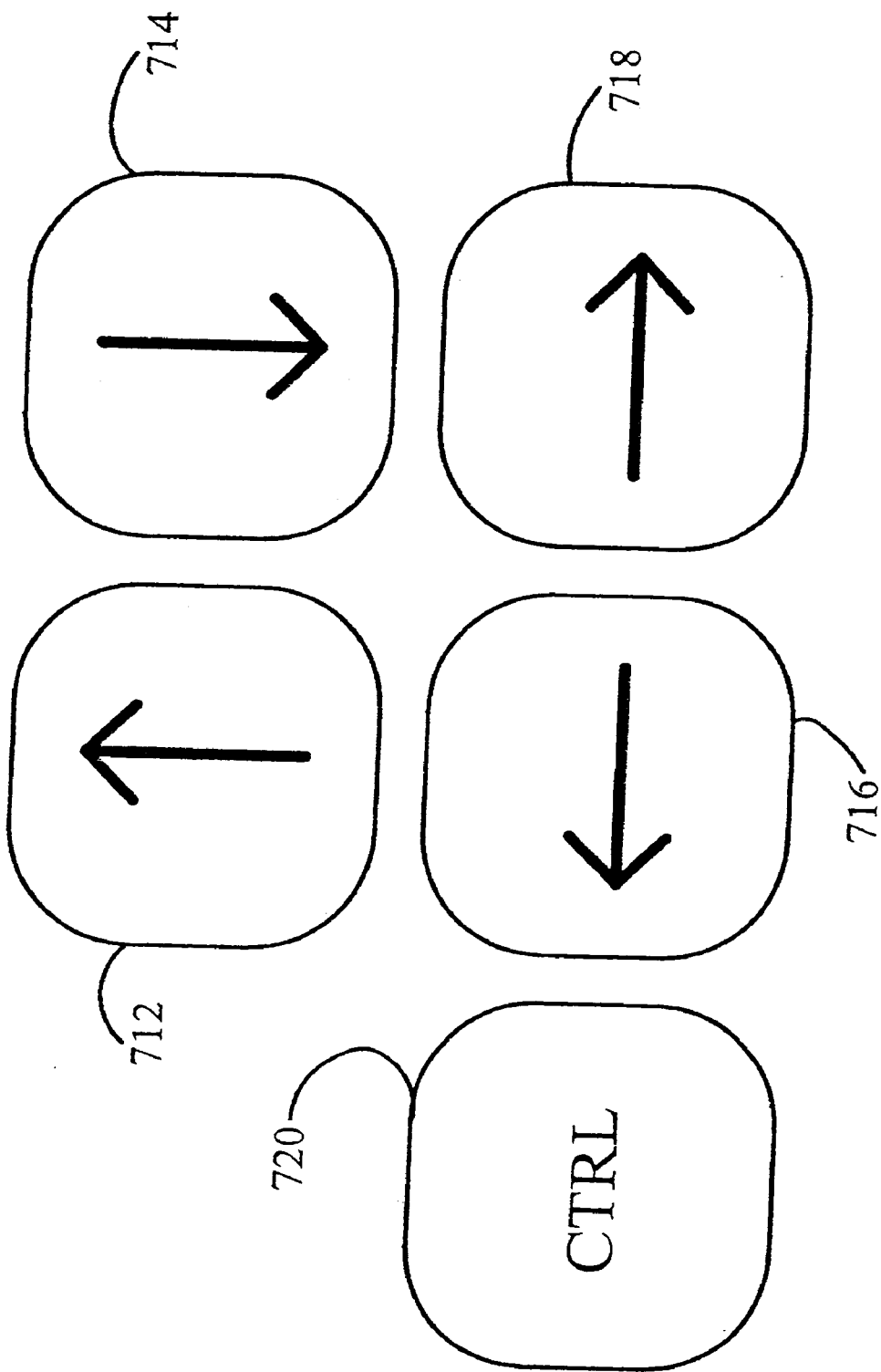
FIG. 14 shows a unitary control keypad for use in conjunction with the GUI of FIGS. 15a–15b.

FIG. 14 shows the unitary, directional keypad which provides a single operating position from which to control the ultrasonic imaging operations. Referring to FIG. 14, an up arrow key 712 and a down arrow key 714 allow a user to scroll through the qualitative ultrasonic imaging operations of the system, as will be described further below. A left arrow key 716 and a right arrow key 718 allow a user to select quantitative parameters corresponding to the ultrasonic imaging operation selected. As described above, the quantitative parameters may be in a range of discrete values, or may span a continuum. A control key 720, employed in conjunction with the up arrow key 712 or down arrow key 714 allows an operator to toggle between two control tabs depicted in FIGS. 15a and 15b, as will be described further below. Since all keys employed in controlling and selecting the ultrasonic imaging operations are accessible from a common operating position, an operator may focus on the ultrasonic image of the subject and on the hand-held probe, and need not be distracted by unwieldy controls. Traditional directional keypads allow only directional control to be applied by the directional keypads, and do not allow both qualitative and quantitative selection of operations from a common, unitary operating position accessible by a single hand.

Figures 15A, 15B:
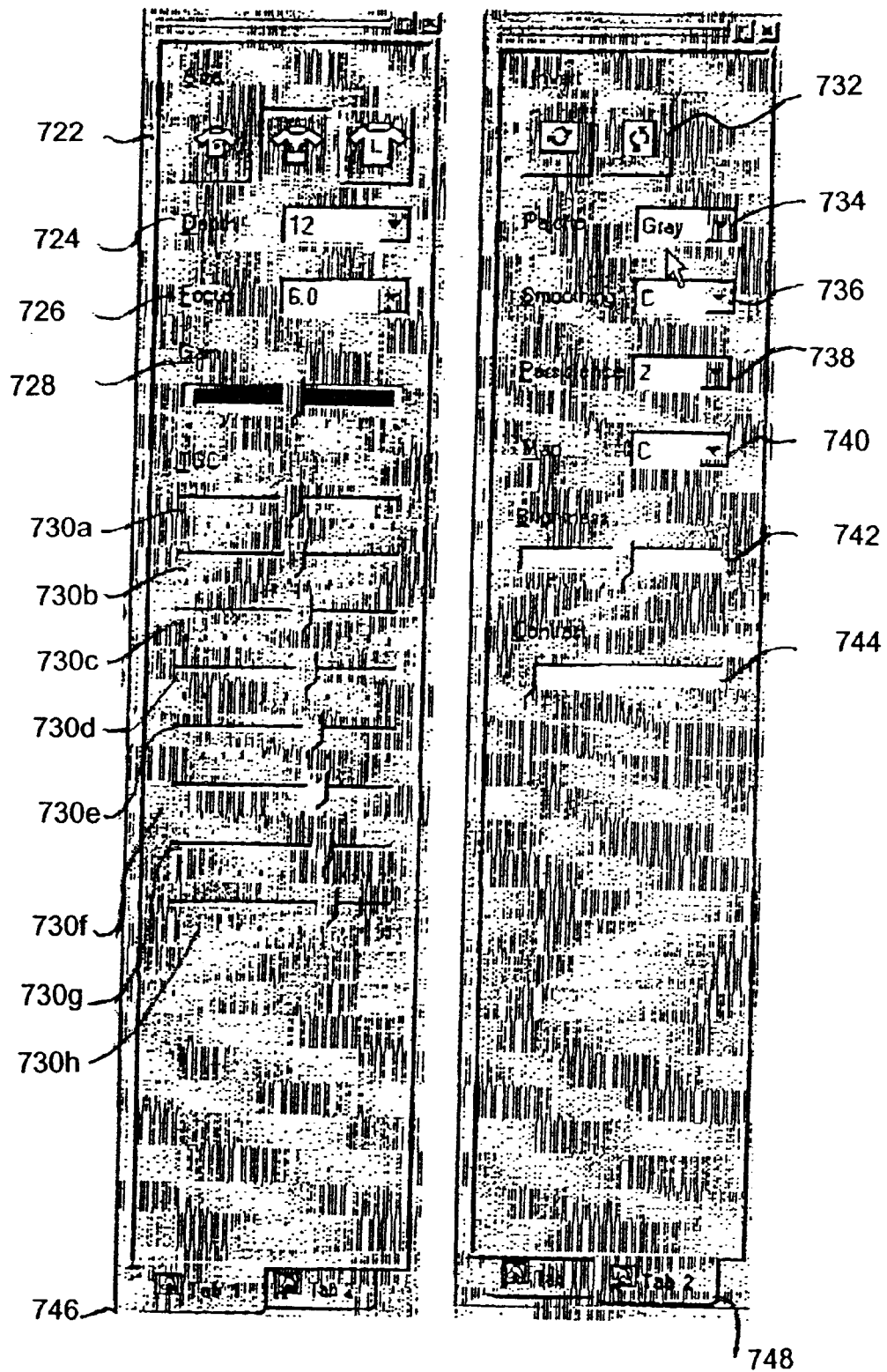
FIG. 15a shows a graphical user interface (GUI) for controlling the scanning operations of the ultrasonic imaging system.
FIG. 15b shows a graphical user interface (GUI) for controlling the processing operations of the ultrasonic imaging system.

FIGS. 15a and 15b show qualitative and quantitative selection of ultrasonic imaging operations via invoking the unitary directional keypad of FIG. 14. Referring to FIG. 15a, ultrasonic imaging operations applicable to scanning are shown. The scanning operations are directed at active acquisition of real-time, dynamic ultrasonic image data, and are typically applied as the hand-held probe is manipulated over the subject imaging area. A size operation 722 sets a series of predetermined defaults for other ultrasonic imaging operations. A small, medium, or large subject may be selected via the left and right arrow keys 716, 718 (FIG. 14). A depth operation 724 allows selection of a depth parameter via the arrow keys 716, 718. Focus is controlled by a focus 726 operation. Gain 728 control adjusts the TGC for all TGC settings 730a–730h. TGC operations 730a–730f adjusts amplification of return signals at varying depths, ranging from the least depth 730a to greatest depth 730h, via the arrow keys 716–718.

Referring to FIG. 15b, ultrasonic imaging operations applicable to processing are shown. The processing operations may be applied to static real-time or frozen images. An inversion operation is controlled by the inversion 732 selection, and rotates the image via the arrow keys 716, 718 (FIG. 14). Palate, smoothing, persistence, and mapping 734, 736, 738, and 740 respectively are selected via the up and down arrow keys 712, 714, and parameters selected via the arrow keys 716, 718 (FIG. 14). Brightness and contrast scales are selected via sliders 742 and 744, respectively, and are changed using arrow keys 716, 718.

Figure 16:
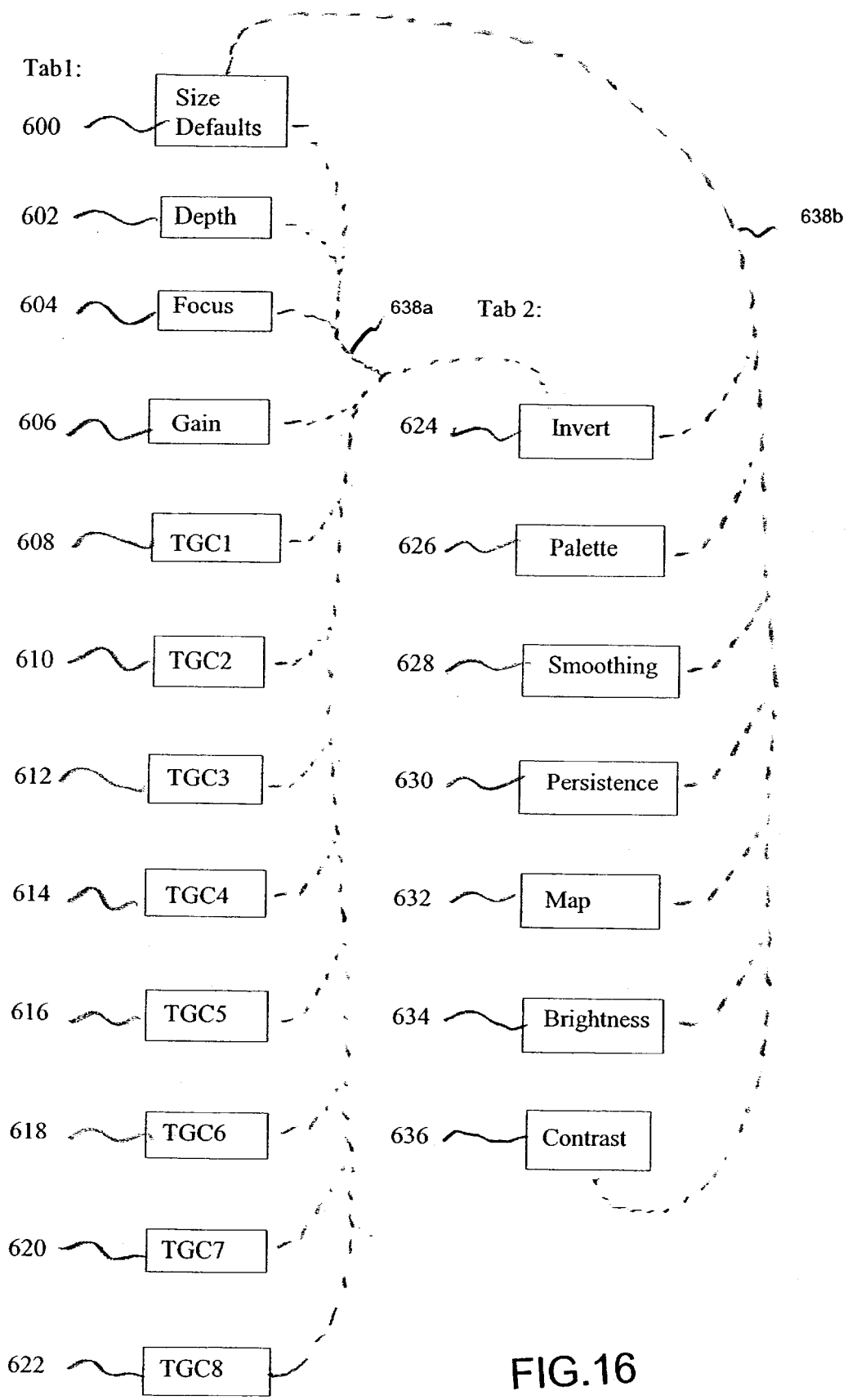
FIG. 16 shows a state diagram corresponding to the GUI of FIGS. 15a–15b.

FIG. 16 shows a state diagram depicting transition between the ultrasonic imaging operations depicted in FIGS. 15a and 15b. Referring to FIGS. 1, 14, and 16, the Tab 746 operations are selected via the up and down arrow keys 712, 714 and transition according to the following state sequence: size 600, depth 602, focus 604, Gain 606, and TGC degrees 608, 610, 612, 614, 616, 618, 620 and 622. Similarly, the Tab2 operations are selected according to the following sequence: invert 624, palette 626, smoothing 628, persistence 630, map 632, brightness 634, and contrast 636. As indicated above, selection of operations may be toggled between Tab1 746 and Tab2 748 using control key 720 and arrow keys 712, 714.

The scanning operations shown in FIG. 15a are displayed on Tab1 746, as shown in FIG. 13. The processing operations shown in FIG. 15b are displayed and selected on Tab2, as shown in FIG. 13. Referring again to FIG. 14, control is toggled between Tab1 746 and Tab2 748 using a combination of the control key 720 and either the up or down arrow keys 712, 714, as shown by dotted lines 638a and 638b.

In general the use of medical ultrasound systems requires the user to have significant training and regular practice to keep skills at a high level. Another embodiment of the invention involves providing the user with an intuitive and simple way to use interface, and with the ability to quickly and automatically set imaging parameters based on a software module. This enables general medical personnel with limited ultrasound experience to obtain diagnostic-quality images without having to adjust the controls. The "Quick Look" feature provides the user with a very simple mechanism of image optimization. It allows the user to simply adjust the image so as to obtain appropriate diagnostic image quality with one push of one button.

The benefits of programmed image parameters are many. The user no longer is required to adjust multiple controls in order to obtain a good image. Exams may be performed in a shorter period of time as a result. The use of this feature also results in more uniform images, regardless of the skills and expertise of the user. This approach is advantageous when performing exams under adverse circumstances such as emergency medical procedures performed in ambulances or remote locations.

The procedure involves the use of predefined histograms. Separate histograms are provided for different anatomical structures that are to be examined. The user chooses a structure, similar to the existing method of choosing a preset. Once the structure is chosen, the user places the transducer on the area of interest in the scanning window. At that time, pressing the selected control button triggers the system to adjust the system contrast and brightness control values so that a histogram of the gray levels in the image closely matches the corresponding pre-defined histogram for that structure. The result is an image of diagnostic image quality that is easily recreated.

The procedure is highly dependent upon the brightness and contrast controls. As a result, a preferred embodiment provides an independent control which allows the user to adjust for ambient lighting changes. In many applications the programmed parameters gets the user very close, but they may choose to fine tune the contrast and brightness.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for controlling an ultrasonic imaging system comprising:
   defining a plurality of ultrasonic imaging operations in a computer readable medium;
   defining a range of values corresponding to each of the ultrasonic imaging operations in the computer readable medium;
   selecting, via a first control, one of the plurality of ultrasonic imaging operations; in the computer readable medium;
   selecting, via a second control, a parameter in the range of values corresponding to the selected ultrasonic imaging operation; and
   applying, via the ultrasonic imaging system, the selected ultrasonic imaging operation employing the selected parameter, the first control and the second control being located and operable from a unitary interface.

2. The method of claim 1 further comprising applying the ultrasonic imaging operation to ultrasonic image data gathered by the ultrasonic imaging system.

3. The method of claim 1 further comprising using a non-dominant hand to operate and control the unitary interface.

4. The method of claim 3 wherein the non-dominant hand remains at the common operating position on the unitary interface throughout a series of ultrasonic imaging operations.

5. The method of claim 1 further comprising providing a common operating position corresponding to a control keypad in the unitary interface being accessible from a single hand.

6. The method of claim 1 further comprising selecting another ultrasonic imaging operation via the first control and selecting another parameter via the second control in the range of values corresponding to the selected another ultrasonic imaging operation from the same unitary interface.

7. The method of claim 6 further comprising selecting a series of ultrasonic imaging operations from the unitary interface and further comprising executing no extraneous operations from another operating position.

8. The method of claim 1 wherein the first control is a qualitative control.

9. The method of claim 1 wherein the second control is a quantitative control.

10. The method of claim 1 wherein the range is a series of discrete values.

11. The method of claim 1 wherein the range is a continuum.

12. The method of claim 1 wherein the ultrasonic imaging operations include ultrasonic image scanning operations and ultrasonic image processing operations.

13. The method of claim 12 wherein the ultrasonic image scanning operations are applicable to dynamic ultrasonic image data.

14. The method of claim 12 wherein the ultrasonic image processing operations are applicable to static and dynamic ultrasonic image data.

15. The method of claim 12 wherein the ultrasonic image scanning operations include image processing operations selected from the group consisting of size, depth, focus, gain, Time Gain Compensation (TGC) and TGC lock.

16. The method of claim 12 wherein the ultrasonic image processing operations include image processing operations selected from the group consisting of view, inversion palette, smoothing, persistence, map, and contrast.

17. A computer readable medium having stored therein instructions for causing a central processing unit to execute the method of claim 1.

18. A system for controlling ultrasonic imaging comprising:
- an ultrasonic imaging controller operable to apply a plurality of ultrasonic imaging operations, the controller having a plurality of instructions for processing a plurality of image parameters to obtain ultrasound images;
- a user input device operable to provide selection input in response to a first user control, and further operable to provide parameters in response to a second user control, the user input device connected to the first user control and the second user control from a common operating position; and
- a graphical user interface (GUI) operable to receive the selection input corresponding to at least one of the ultrasonic imaging operations, and further operable to receive parameters in a range corresponding to the selected ultrasonic imaging operations.

19. The system of claim 18 wherein the ultrasonic imaging controller is further operable to apply the ultrasonic imaging operation to ultrasonic image data gathered by a hand held probe in an ultrasonic imaging system.

20. The system of claim 18 wherein the common operating position is adapted to be accessible from a non-dominant hand.

21. The system of claim 18 wherein the common operating position corresponds to a control keypad accessible from a single hand.

22. The system of claim 18 wherein the user input device is operable to provide selection input and corresponding to another ultrasonic imaging operation via the first user control and further operable to provide another parameter via the second user control in the range of values corresponding to the selected another ultrasonic imaging operation from the same common operating position.

23. The system of claim 22 wherein the user input device is further operable for selecting a series of ultrasonic imaging operations from the common operating position and further comprising executing no extraneous operations from another operating position.

24. The system of claim 18 wherein a non-dominant hand remains at the common operating position throughout the series of ultrasonic imaging operations.

25. The system of claim 18 wherein the first user control is a qualitative control.

26. The system of claim 18 wherein the second user control is a quantitative control.

27. The system of claim 18 wherein the range is a series of discrete values.

28. The system of claim 18 wherein the range is a continuum.

29. The system of claim 18 wherein the ultrasonic imaging controller is further operable to apply ultrasonic imaging operations including ultrasonic image scanning operations and ultrasonic image processing operations.

30. The system of claim 29 wherein the ultrasonic imaging controller is further operable to apply ultrasonic image scanning operations applicable to dynamic ultrasonic image data.

31. The system of claim 29 wherein the ultrasonic imaging controller is further operable to apply ultrasonic image processing operations applicable to static and dynamic ultrasonic image data.

32. A computer readable medium including instructions for controlling an ultrasonic imaging system comprising:
- defining a plurality of ultrasonic imaging operations;
- defining a range of values corresponding to each of the ultrasonic imaging operations;
- selecting, via a first control, one of the plurality of ultrasonic imaging operations;
- selecting, via a second control, a parameter in the range of values corresponding to the selected ultrasonic imaging operation; and
- applying, via the ultrasonic imaging system, the selected ultrasonic imaging operation employing the selected parameter, the first control and the second control being operable from a common operating position.

33. A computer readable data transmission medium having program code for controlling an ultrasonic imaging system comprising:
- a first portion of program code for defining a plurality of ultrasonic imaging operations;
- a second portion of program code for defining a range of values corresponding to each of the ultrasonic imaging operations;
- a third portion of program code for selecting, via a first control, one of the plurality of ultrasonic imaging operations;
- a fourth portion of program code for selecting, via a second control, a parameter in the range of values corresponding to the selected ultrasonic imaging operation; and
- a fifth portion of program code for applying, via the ultrasonic imaging system, the selected ultrasonic imaging operation employing the selected parameter, the first control and the second control being operable from a common operating position.

34. A computer program product for controlling and for displaying ultrasonic images in an ultrasonic imaging system, the computer program product comprising a computer usable medium having computer readable code therein, including program code which:
- defines a plurality of ultrasonic imaging operations;
- defines a range of values corresponding to each of the ultrasonic imaging operations;
- selects, via a first control, one of the plurality of ultrasonic imaging operations;
- selects, via a second control, a parameter in the range of values corresponding to the selected ultrasonic imaging operation; and
- applies, via the ultrasonic imaging system, the selected ultrasonic imaging operation employing the selected parameter, the first control and the second control being operable from a common operating position.

35. A graphical user interface for controlling and displaying ultrasound images and data, comprising:
- a graphical user interface element for displaying an ultrasonic image of a region of interest;
- a graphical user interface element for selecting one of a plurality of ultrasonic imaging operations;
- a graphical user interface element for selecting quantitative parameters corresponding to the ultrasonic imaging operations; and
- a graphical user interface element for controlling the selection of the graphical user interface elements.

* * * * *